(12) United States Patent
Hemmait-Brivanlou et al.

(10) Patent No.: US 6,291,651 B1
(45) Date of Patent: Sep. 18, 2001

(54) ANTIBODIES TO A NOVEL SRC-FAMILY KINASE

(75) Inventors: Ali Hemmait-Brivanlou; Daniel C. Weinstein, both of New York, NY (US)

(73) Assignee: The Rockerfeller University, New York, NY (US)

( * ) Notice: Subject to any disclaimer, the term of this patent is extended or adjusted under 35 U.S.C. 154(b) by 0 days.

(21) Appl. No.: 09/228,603

(22) Filed: Jan. 12, 1999

Related U.S. Application Data

(60) Provisional application No. 60/071,269, filed on Jan. 13, 1998.

(51) Int. Cl.[7] .............................. C07K 16/00; C12N 5/12; C12P 21/08
(52) U.S. Cl. .................................... 530/387.3; 530/387.9; 530/388.26; 530/389.1; 435/331; 435/338
(58) Field of Search .............................. 530/387.3, 387.9, 530/388.26, 389.1; 435/338, 331

(56) References Cited

FOREIGN PATENT DOCUMENTS

WO 93/14193 * 7/1993 (WO) .

OTHER PUBLICATIONS

Huesgen, A, et al., The immune response against the ASV–coded src–gene product in syngenic mice. J. Gen. Virol. 48:401–406, 1980.*
Harlow, E and Lane, D, Antibodies: A Laboratory Manual. Cold Spring Harbor Press, p. 76, 1980.*
Amaya et al, 1991, Cell, 66:257–70.
Brown and Cooper, 1996, Biochimica et Biophysica Acta. 1287:121–49.
Collett and Steele, 1992, Dev Biol, 152:194–8.
Cornell and Kimelman, 1994, Development, 120:453–62.
Hemmati–Brivanlou, 1995, Nature, 376:331–3.
Jones and Woodland, 1987, Development, 101:557–63.
Kintner and Melton, 1987, Development, 99:311–25.
Klein and Melton, 1994, Endocr Rev, 15:326–41.
Kretzachmar et al, 1997, Nature, 389:618–22.
Labonne and Whitman, 1997, Dev Biol, 183:9–20.
Lagna et al, 1996, Nature, 383:832–6.
Lowenstein et al, 1992, Cell, 70:431–42.
Massague et al, 1997, TICB, 7:187–92.
Mohun et al, 1984,Nature, 311:716–21.
Rozakis–Adcock et al, 1992, Nature, 360:689–92.
Sasai et al, 1994, Cell, 79:779–90.
Smith et al, 1991, Cell, 67:79–87.
Steele, 1985, Nucleic Acids Res, 13:1747–61.
Tanaka et al, 1997, Proc Natl Acad Sci USA, 94:4493–8.
Tang et al, 1995, Cell, 80:473–83.
Theil, 1990, J Biol Chem, 265:4771–4.
Weiss and Littman, 1994, Cell, 76:263–74.
Wright et al, 1990, Development, 109:225–34.
Zeigler et al, 1989, Mol Cell Biol, 9:2724–7.

* cited by examiner

Primary Examiner—David Saunders
Assistant Examiner—Mary Beth Tung
(74) Attorney, Agent, or Firm—Darby & Darby

(57) ABSTRACT

The present invention provides a unique src-family kinase (SFK) that plays a key role in the transformation of early-stage embryonic cells to mesodermal cells. Furthermore, this src-family kinase is likely to be a proto-oncogene. The nucleic acid and amino acid sequences are disclosed.

21 Claims, 14 Drawing Sheets uninjected

27AlJA (laloo)

FIG. 1C-1

| | | | | | | | |
|---|---|---|---|---|---|---|---|
| ATG GGC TGC ATC AAG TCA AAG GAT TCA AAT ACG ACT GGC AAA AGT CTG | | | | | | | 48 |
| M   G   C   I   K   S   K   D   S   N   T   T   G   K   S   L | | | | | | | |
| GGA CCT CCG GAA AGC ACC CAA ACC CAT TAT GTG AAG GAC CCA ACA TCT | | | | | | | 96 |
| G   P   P   E   S   T   Q   T   H   Y   V   K   D   P   T   S | | | | | | | |
| ACA GTA ACT ATG ACT AAA CCT GAA AGA TCA TCT AAG CAC CCC AGA GAG | | | | | | | 144 |
| T   V   T   M   T   K   P   E   R   S   S   K   H   P   R   E | | | | | | | |
| GAA GGG CAA GAA GAA GTG CTG GTC CTG GCT TTG TAT GAC TAT GAT GGA | | | | | | | 192 |
| E   G   Q   E   E   V   L   V   L   A   L   Y   D   Y   D   G | | | | | | | |
| GTC CAC CCT GGG GAT CTG ACT TTT AGG AAA GGG GAC CAT CTC CTG CTA | | | | | | | 240 |
| V   H   P   G   D   L   T   F   R   K   G   D   H   L   L   L | | | | | | | |
| AAG AAA GAG TCA GGG GAG TGG TGG GAA GCA TGT CTA ATT TCC ACT GGT | | | | | | | 288 |
| K   K   E   S   G   E   W   W   E   A   C   L   I   S   T   G | | | | | | | |
| GAA GAA GGC TTT GTT CCC AGT AAC TAT GTA GCG TAT TTC AAT TCC CTG | | | | | | | 336 |
| E   E   G   F   V   P   S   N   Y   V   A   Y   F   N   S   L | | | | | | | |

FIG. IC-2

```
GAA TCT GAA GAG TGG TAC TTT AAA GGC ATG AGC CGG AAG GAA GCT GAA    384
 E   S   E   E   W   Y   F   K   G   M   S   R   K   E   A   E

AGG CAG CTG CTA TCT CCT GTT AAT AAA AGT GGG GCT TTC ATG ATC CGA    432
 R   Q   L   L   S   P   V   N   K   S   G   A   F   M   I   R

GAC AGT GAG ACA ATG AAA GGT TGT TTC TCC CTC TCT GTG CGA GAC TCA    480
 D   S   E   T   M   K   G   C   F   S   L   S   V   R   D   S

GGG GAC ACT GTG AAA CAT TAC AAA ATT CGC ACA CTC GAT GAT GGA GGT    528
 G   D   T   V   K   H   Y   K   I   R   T   L   D   D   G   G

TTC ATT TCT ACA CGG ATC CCT TTT CCT TCT TTG CCA GAG CTG GTA        576
 F   I   S   T   R   I   P   F   P   S   L   P   E   L   V

CGC CAT TAT CAA GGT AAA GTG GAT GGC TTG TGT CAG TGC CTT ACA ATA    624
 R   H   Y   Q   G   K   V   D   G   L   C   Q   C   L   T   I

CCA TGC CAA ACT GTG CGT CCA GAG AAA CCA TGG GAA AAG GAT GCC TGG    672
 P   C   Q   T   V   R   P   E   K   P   W   E   K   D   A   W
```

FIG. 1C-3

```
GAG ATC CCG CGC GAG TCA CTG TCA CTG CAG AAG AAG CTT GGA GCT GGA   720
 E   I   P   R   E   S   L   S   L   Q   K   K   L   G   A   G

CAG TTT GGG GAT GTT TGG TTG GCC ATG TAC AAT GGA CAC ACA AAA GTA   768
 Q   F   G   D   V   W   L   A   M   Y   N   G   H   T   K   V

GCT GTA AAA ACA ATG AAG CCA GGC AGC ATG TCC CCC GGT GCC TTC CTT   816
 A   V   K   T   M   K   P   G   S   M   S   P   G   A   F   L

GAA GAG GCA AAT CTG ATG AAG AGC TTG CAG CAT GAC CGG CTG GTG CGG   864
 E   E   A   N   L   M   K   S   L   Q   H   D   R   L   V   R

TTG CAT GCC GTT GTG ACT CAG GGG GAA CCA ATA TAT ATC ATT ACT GAG   912
 L   H   A   V   V   T   Q   G   E   P   I   Y   I   I   T   E

TAT ATG CAA AAG GGC AGT TTG CTG GAT TTC CTG AAA AGT GAA GAA GGT   960
 Y   M   Q   K   G   S   L   L   D   F   L   K   S   E   E   G

AGC GAC CAA CCT CTG ATT CAA CTC ATT GAC TTC TCT GCC CAG ATT GCA   1008
 S   D   Q   P   L   I   Q   L   I   D   F   S   A   Q   I   A
```

FIG. IC-4

```
GAA GGA ATG TGG TTT ATT GAG CAA AGG AAT TAT ATT CAC CGT GAT CTG   1056
 E   G   M   W   F   I   E   Q   R   N   Y   I   H   R   D   L

AGG GCA GCA AAC TGC CTG GTA TCA GAA ACT TTG TTG TGC AAA ATA GCA   1104
 R   A   A   N   C   L   V   S   E   T   L   L   C   K   I   A

GAC TTT GGG CTG GCC CGA GTG ATA GAG GAC AGC GAG TAT ACT GCC AGG   1152
 D   F   G   L   A   R   V   I   E   D   S   E   Y   T   A   R

GAA GGT ACC AAA TTT CCC ATC AAG TGG ACA TCC CTG GAG GCT GCC AAT   1200
 E   G   T   K   F   P   I   K   W   T   S   L   E   A   A   N

TAT GGC TCT TTT ACT ATC AAG TCA GAT GTA TGG TCA TTT GGT GTA TTG   1248
 Y   G   S   F   T   I   K   S   D   V   W   S   F   G   V   L

CTA ACT GAA ATA ATA ACA TAT GGG AGG ACT CCA TAT CCA GGT ATG TCC   1296
 L   T   E   I   I   T   Y   G   R   T   P   Y   P   G   M   S

AAC TCG GAG GTA ATT ACA GCC CTT GAG CGT GGT TAT CGC ATG CCG TGT   1344
 N   S   E   V   I   T   A   L   E   R   G   Y   R   M   P   C
```

FIG. IC-5

```
CCC AGC ACT TGT CCA AAA GAG CTC TAC AGC ATC ATG CTC CAG TGT TGG    1392
 P   S   T   C   P   K   E   L   Y   S   I   M   L   Q   C   W

CAG CAG GAC CCT GAG CAA CGG CCA ACG TTT GAA TAT TTA CAG AGC ATC    1440
 Q   Q   D   P   E   Q   R   P   T   F   E   Y   L   Q   S   I

CTA GAG GAC TTC TTT ACT GCC ACT GAA ACA CAG TAC CAG GCA CAA CCT    1488
 L   E   D   F   F   T   A   T   E   T   Q   Y   Q   A   Q   P

TAA                                                                1491
```

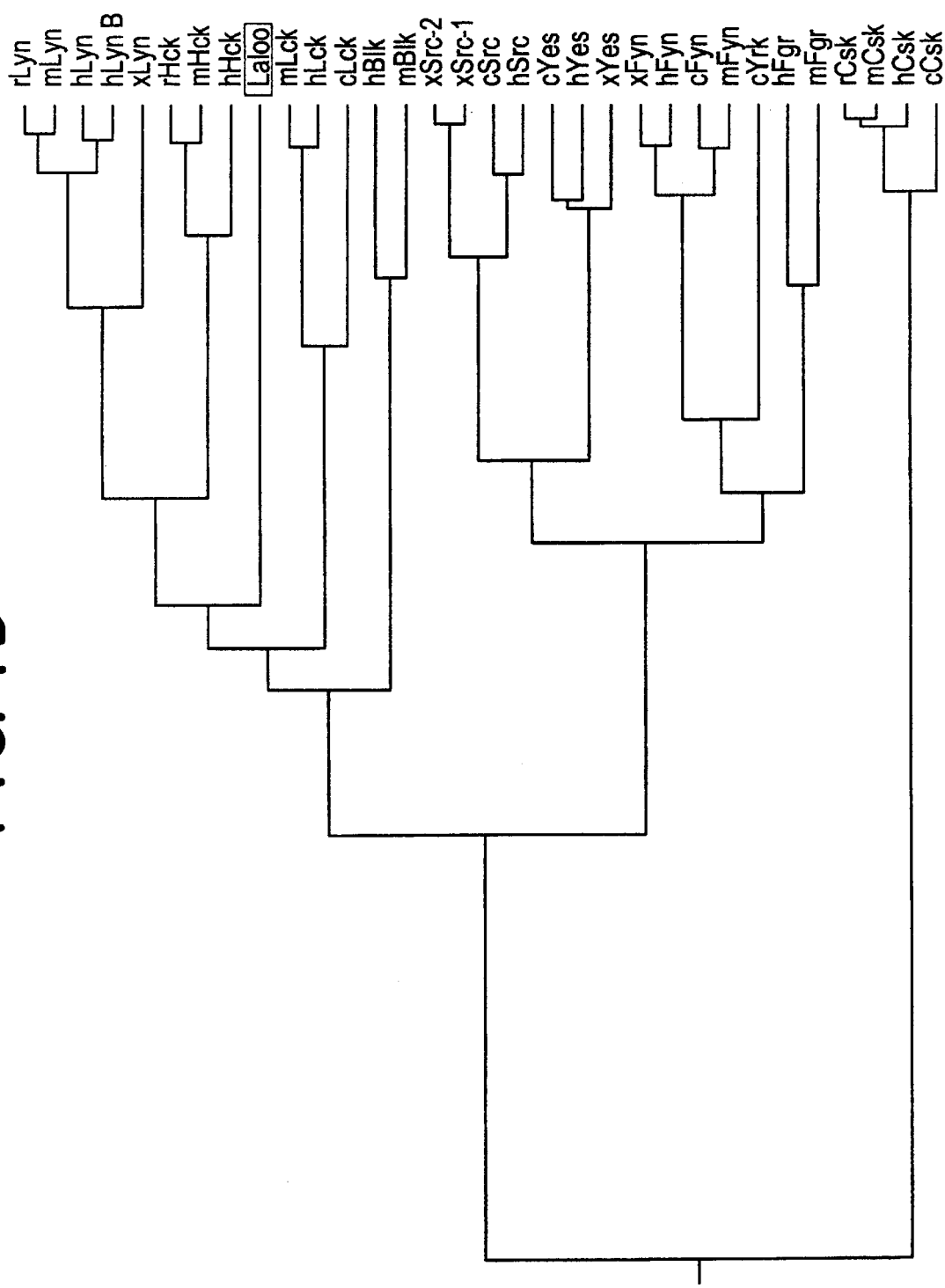
FIG. ID stage 11.5 stage 22

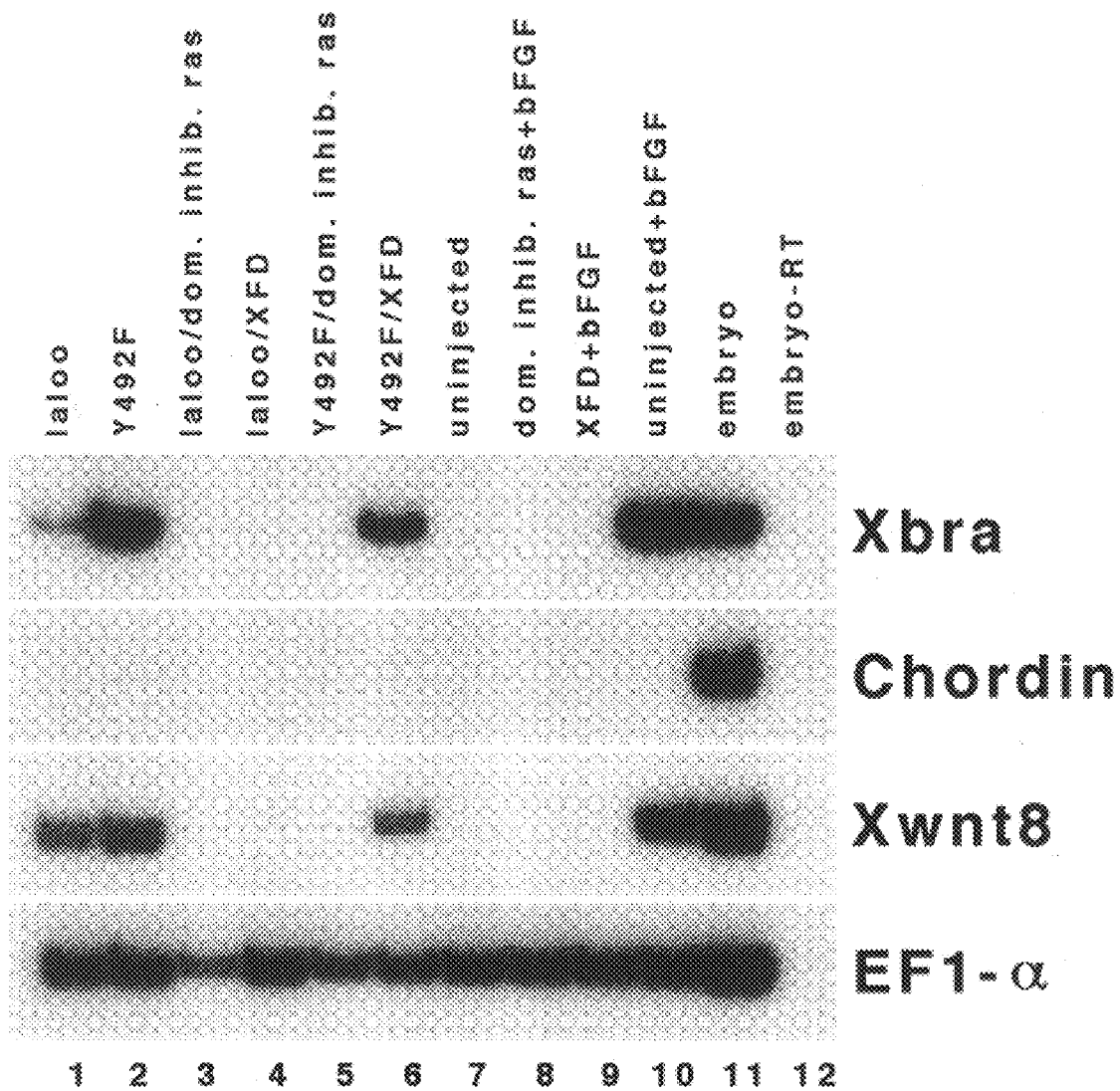

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 1491 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (ix) FEATURE:
      (A) NAME/KEY: CDS
      (B) LOCATION: 1..1491

(xi) SEQUENCE DESCRIPTION: SEQ ID NO:1:

```
ATG GGC TGC ATC AAG TCA AAG GAT TCA AAT ACG ACT GGC AAA AGT CTG        48
Met Gly Cys Ile Lys Ser Lys Asp Ser Asn Thr Thr Gly Lys Ser Leu
 1               5                  10                  15

GGA CCT CCG GAA AGC ACC CAA ACC CAT TAT GTG AAG GAC CCA ACA TCT        96
Gly Pro Pro Glu Ser Thr Gln Thr His Tyr Val Lys Asp Pro Thr Ser
             20                  25                  30

ACA GTA ACT ATG ACT AAA CCT GAA AGA TCA TCT AAG CAC CCC AGA GAG       144
Thr Val Thr Met Thr Lys Pro Glu Arg Ser Ser Lys His Pro Arg Glu
         35                  40                  45

GAA GGG CAA GAA GAA GTG GTC CTG CTG GCT TTG TAT GAC TAT GAT GGA       192
Glu Gly Gln Glu Glu Val Val Leu Leu Ala Leu Tyr Asp Tyr Asp Gly
     50                  55                  60

GTC CAC CCT GGG GAT CTG ACT TTT AGG AAA GGG GAC CAT CTC CTG CTA       240
Val His Pro Gly Asp Leu Thr Phe Arg Lys Gly Asp His Leu Leu Leu
 65                  70                  75                  80

AAG AAA GAG TCA GGG GAG TGG TGG GAA GCA TGT CTA ATT TCC ACT GGT       288
Lys Lys Glu Ser Gly Glu Trp Trp Glu Ala Cys Leu Ile Ser Thr Gly
                 85                  90                  95

GAA GAA GGC TTT GTT CCC AGT AAC TAT GTA GCG TAT TTC AAT TCC CTG       336
Glu Glu Gly Phe Val Pro Ser Asn Tyr Val Ala Tyr Phe Asn Ser Leu
             100                 105                 110
```

```
GAA TCT GAA GAG TGG TAC TTT AAA GGC ATG AGC CGG AAG GAA GCT GAA      384
Glu Ser Glu Glu Trp Tyr Phe Lys Gly Met Ser Arg Lys Glu Ala Glu
    115                 120                 125

AGG CAG CTG CTA TCT CCT GTT AAT AAA AGT GGG GCT TTC ATG ATC CGA      432
Arg Gln Leu Leu Ser Pro Val Asn Lys Ser Gly Ala Phe Met Ile Arg
130                 135                 140

GAC AGT GAG ACA ATG AAA GGT TGT TTC TCC CTC TCT GTG CGA GAC TCA      480
Asp Ser Glu Thr Met Lys Gly Cys Phe Ser Leu Ser Val Arg Asp Ser
145                 150                 155                 160

GGG GAC ACT GTG AAA CAT TAC AAA ATT CGC ACA CTC GAT GAT GGA GGT      528
Gly Asp Thr Val Lys His Tyr Lys Ile Arg Thr Leu Asp Asp Gly Gly
                165                 170                 175

TTC TTC ATT TCT ACA CGG ATC CCT TTT CCT TCT TTG CCA GAG CTG GTA      576
Phe Phe Ile Ser Thr Arg Ile Pro Phe Pro Ser Leu Pro Glu Leu Val
            180                 185                 190

CGC CAT TAT CAA GGT AAA GTG GAT GGC TTG TGT CAG TGC CTT ACA ATA      624
Arg His Tyr Gln Gly Lys Val Asp Gly Leu Cys Gln Cys Leu Thr Ile
        195                 200                 205

CCA TGC CAA ACT GTG CGT CCA GAG AAA CCA TGG GAA AAG GAT GCC TGG      672
Pro Cys Gln Thr Val Arg Pro Glu Lys Pro Trp Glu Lys Asp Ala Trp
210                 215                 220

GAG ATC CCG CGC GAG TCA CTG TCA CTG CAG AAG AAG CTT GGA GCT GGA      720
Glu Ile Pro Arg Glu Ser Leu Ser Leu Gln Lys Lys Leu Gly Ala Gly
225                 230                 235                 240

CAG TTT GGG GAT GTT TGG TTG GCC ATG TAC AAT GGA CAC ACA AAA GTA      768
Gln Phe Gly Asp Val Trp Leu Ala Met Tyr Asn Gly His Thr Lys Val
                245                 250                 255

GCT GTA AAA ACA ATG AAG CCA GGC AGC ATG TCC CCC GGT GCC TTC CTT      816
Ala Val Lys Thr Met Lys Pro Gly Ser Met Ser Pro Gly Ala Phe Leu
            260                 265                 270

GAA GAG GCA AAT CTG ATG AAG AGC TTG CAG CAT GAC CGG CTG GTG CGG      864
Glu Glu Ala Asn Leu Met Lys Ser Leu Gln His Asp Arg Leu Val Arg
        275                 280                 285

TTG CAT GCC GTT GTG ACT CAG GGG GAA CCA ATA TAT ATC ATT ACT GAG      912
Leu His Ala Val Val Thr Gln Gly Glu Pro Ile Tyr Ile Ile Thr Glu
290                 295                 300

TAT ATG CAA AAG GGC AGT TTG CTG GAT TTC CTG AAA AGT GAA GAA GGT      960
Tyr Met Gln Lys Gly Ser Leu Leu Asp Phe Leu Lys Ser Glu Glu Gly
305                 310                 315                 320

AGC GAC CAA CCT CTG ATT CAA CTC ATT GAC TTC TCT GCC CAG ATT GCA     1008
Ser Asp Gln Pro Leu Ile Gln Leu Ile Asp Phe Ser Ala Gln Ile Ala
                325                 330                 335

GAA GGA ATG TGG TTT ATT GAG CAA AGG AAT TAT ATT CAC CGT GAT CTG     1056
Glu Gly Met Trp Phe Ile Glu Gln Arg Asn Tyr Ile His Arg Asp Leu
            340                 345                 350

AGG GCA GCA AAC TGC CTG GTA TCA GAA ACT TTG TTG TGC AAA ATA GCA     1104
Arg Ala Ala Asn Cys Leu Val Ser Glu Thr Leu Leu Cys Lys Ile Ala
        355                 360                 365

GAC TTT GGG CTG GCC CGA GTG ATA GAG GAC AGC GAG TAT ACT GCC AGG     1152
Asp Phe Gly Leu Ala Arg Val Ile Glu Asp Ser Glu Tyr Thr Ala Arg
370                 375                 380

GAA GGT ACC AAA TTT CCC ATC AAG TGG ACA TCC CTG GAG GCT GCC AAT     1200
Glu Gly Thr Lys Phe Pro Ile Lys Trp Thr Ser Leu Glu Ala Ala Asn
385                 390                 395                 400

TAT GGC TCT TTT ACT ATC AAG TCA GAT GTA TGG TCA TTT GGT GTA TTG     1248
Tyr Gly Ser Phe Thr Ile Lys Ser Asp Val Trp Ser Phe Gly Val Leu
                405                 410                 415

CTA ACT GAA ATA ATA ACA TAT GGG AGG ACT CCA TAT CCA GGT ATG TCC     1296
Leu Thr Glu Ile Ile Thr Tyr Gly Arg Thr Pro Tyr Pro Gly Met Ser
            420                 425                 430
```

```
AAC TCG GAG GTA ATT ACA GCC CTT GAG CGT GGT TAT CGC ATG CCG TGT    1344
Asn Ser Glu Val Ile Thr Ala Leu Glu Arg Gly Tyr Arg Met Pro Cys
        435                 440                 445

CCC AGC ACT TGT CCA AAA GAG CTC TAC AGC ATC ATG CTC CAG TGT TGG    1392
Pro Ser Thr Cys Pro Lys Glu Leu Tyr Ser Ile Met Leu Gln Cys Trp
        450                 455                 460

CAG CAG GAC CCT GAG CAA CGG CCA ACG TTT GAA TAT TTA CAG AGC ATC    1440
Gln Gln Asp Pro Glu Gln Arg Pro Thr Phe Glu Tyr Leu Gln Ser Ile
465                 470                 475                 480

CTA GAG GAC TTC TTT ACT GCC ACT GAA ACA CAG TAC CAG GCA CAA CCT    1488
Leu Glu Asp Phe Phe Thr Ala Thr Glu Thr Gln Tyr Gln Ala Gln Pro
                485                 490                 495

TAA                                                                1491

(2) INFORMATION FOR SEQ ID NO:2:

(i) SEQUENCE CHARACTERISTICS:
        (A) LENGTH: 496 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Cys Ile Lys Ser Lys Asp Ser Asn Thr Thr Gly Lys Ser Leu
1               5                   10                  15

Gly Pro Pro Glu Ser Thr Gln Thr His Tyr Val Lys Asp Pro Thr Ser
                20                  25                  30

Thr Val Thr Met Thr Lys Pro Glu Arg Ser Ser Lys His Pro Arg Glu
            35                  40                  45

Glu Gly Gln Glu Glu Val Val Leu Leu Ala Leu Tyr Asp Tyr Asp Gly
        50                  55                  60

Val His Pro Gly Asp Leu Thr Phe Arg Lys Gly Asp His Leu Leu Leu
65                  70                  75                  80

Lys Lys Glu Ser Gly Glu Trp Trp Glu Ala Cys Leu Ile Ser Thr Gly
                85                  90                  95

Glu Glu Gly Phe Val Pro Ser Asn Tyr Val Ala Tyr Phe Asn Ser Leu
                100                 105                 110

Glu Ser Glu Glu Trp Tyr Phe Lys Gly Met Ser Arg Lys Glu Ala Glu
            115                 120                 125

Arg Gln Leu Leu Ser Pro Val Asn Lys Ser Gly Ala Phe Met Ile Arg
        130                 135                 140

Asp Ser Glu Thr Met Lys Gly Cys Phe Ser Leu Ser Val Arg Asp Ser
145                 150                 155                 160

Gly Asp Thr Val Lys His Tyr Lys Ile Arg Thr Leu Asp Asp Gly Gly
                165                 170                 175

Phe Phe Ile Ser Thr Arg Ile Pro Phe Pro Ser Leu Pro Glu Leu Val
                180                 185                 190

Arg His Tyr Gln Gly Lys Val Asp Gly Leu Cys Gln Cys Leu Thr Ile
            195                 200                 205

Pro Cys Gln Thr Val Arg Pro Glu Lys Pro Trp Glu Lys Asp Ala Trp
        210                 215                 220

Glu Ile Pro Arg Glu Ser Leu Ser Leu Gln Lys Lys Leu Gly Ala Gly
225                 230                 235                 240

Gln Phe Gly Asp Val Trp Leu Ala Met Tyr Asn Gly His Thr Lys Val
                245                 250                 255
```

```
Ala Val Lys Thr Met Lys Pro Gly Ser Met Ser Pro Gly Ala Phe Leu
            260                 265                 270

Glu Glu Ala Asn Leu Met Lys Ser Leu Gln His Asp Arg Leu Val Arg
            275                 280                 285

Leu His Ala Val Val Thr Gln Gly Glu Pro Ile Tyr Ile Ile Thr Glu
290                 295                 300

Tyr Met Gln Lys Gly Ser Leu Leu Asp Phe Leu Lys Ser Glu Glu Gly
305                 310                 315                 320

Ser Asp Gln Pro Leu Ile Gln Leu Ile Asp Phe Ser Ala Gln Ile Ala
                325                 330                 335

Glu Gly Met Trp Phe Ile Glu Gln Arg Asn Tyr Ile His Arg Asp Leu
            340                 345                 350

Arg Ala Ala Asn Cys Leu Val Ser Glu Thr Leu Leu Cys Lys Ile Ala
            355                 360                 365

Asp Phe Gly Leu Ala Arg Val Ile Glu Asp Ser Glu Tyr Thr Ala Arg
            370                 375                 380

Glu Gly Thr Lys Phe Pro Ile Lys Trp Thr Ser Leu Glu Ala Ala Asn
385                 390                 395                 400

Tyr Gly Ser Phe Thr Ile Lys Ser Asp Val Trp Ser Phe Gly Val Leu
                405                 410                 415

Leu Thr Glu Ile Ile Thr Tyr Gly Arg Thr Pro Tyr Pro Gly Met Ser
            420                 425                 430

Asn Ser Glu Val Ile Thr Ala Leu Glu Arg Gly Tyr Arg Met Pro Cys
            435                 440                 445

Pro Ser Thr Cys Pro Lys Glu Leu Tyr Ser Ile Met Leu Gln Cys Trp
450                 455                 460

Gln Gln Asp Pro Glu Gln Arg Pro Thr Phe Glu Tyr Leu Gln Ser Ile
465                 470                 475                 480

Leu Glu Asp Phe Phe Thr Ala Thr Glu Thr Gln Tyr Gln Ala Gln Pro
                485                 490                 495

(2) INFORMATION FOR SEQ ID NO:3:

(i) SEQUENCE CHARACTERISTICS:
        (A) LENGTH: 177 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 1..177

(xi) SEQUENCE DESCRIPTION: SEQ ID NO:3:

GAA GTG GTC CTG CTG GCT TTG TAT GAC TAT GAT GGA GTC CAC CCT GGG      48
Glu Val Val Leu Leu Ala Leu Tyr Asp Tyr Asp Gly Val His Pro Gly
        500                 505                 510

GAT CTG ACT TTT AGG AAA GGG GAC CAT CTC CTG CTA AAG AAA GAG TCA      96
Asp Leu Thr Phe Arg Lys Gly Asp His Leu Leu Leu Lys Lys Glu Ser
    515                 520                 525

GGG GAG TGG TGG GAA GCA TGT CTA ATT TCC ACT GGT GAA GAA GGC TTT    144
Gly Glu Trp Trp Glu Ala Cys Leu Ile Ser Thr Gly Glu Glu Gly Phe
530                 535                 540                 545

GTT CCC AGT AAC TAT GTA GCG TAT TTC AAT TCC                        177
Val Pro Ser Asn Tyr Val Ala Tyr Phe Asn Ser
                550                 555
```

(2) INFORMATION FOR SEQ ID NO:4:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO:4:

```
Glu Val Val Leu Leu Ala Leu Tyr Asp Tyr Asp Gly Val His Pro Gly
 1               5                  10                  15

Asp Leu Thr Phe Arg Lys Gly Asp His Leu Leu Leu Lys Lys Glu Ser
            20                  25                  30

Gly Glu Trp Trp Glu Ala Cys Leu Ile Ser Thr Gly Glu Glu Gly Phe
        35                  40                  45

Val Pro Ser Asn Tyr Val Ala Tyr Phe Asn Ser
    50                  55
```

(2) INFORMATION FOR SEQ ID NO:5:

(i) SEQUENCE CHARACTERISTICS:
        (A) LENGTH: 282 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 1..282

(xi) SEQUENCE DESCRIPTION: SEQ ID NO:5:

```
TGG TAC TTT AAA GGC ATG AGC CGG AAG GAA GCT GAA AGG CAG CTG CTA        48
Trp Tyr Phe Lys Gly Met Ser Arg Lys Glu Ala Glu Arg Gln Leu Leu
 60                  65                  70                  75

TCT CCT GTT AAT AAA AGT GGG GCT TTC ATG ATC CGA GAC AGT GAG ACA        96
Ser Pro Val Asn Lys Ser Gly Ala Phe Met Ile Arg Asp Ser Glu Thr
            80                  85                  90

ATG AAA GGT TGT TTC TCC CTC TCT GTG CGA GAC TCA GGG GAC ACT GTG       144
Met Lys Gly Cys Phe Ser Leu Ser Val Arg Asp Ser Gly Asp Thr Val
        95                 100                 105

AAA CAT TAC AAA ATT CGC ACA CTC GAT GAT GGA GGT TTC TTC ATT TCT       192
Lys His Tyr Lys Ile Arg Thr Leu Asp Asp Gly Gly Phe Phe Ile Ser
    110                 115                 120

ACA CGG ATC CCT TTT CCT TCT TTG CCA GAG CTG GTA CGC CAT TAT CAA       240
Thr Arg Ile Pro Phe Pro Ser Leu Pro Glu Leu Val Arg His Tyr Gln
125                 130                 135

GGT AAA GTG GAT GGC TTG TGT CAG TGC CTT ACA ATA CCA TGC               282
Gly Lys Val Asp Gly Leu Cys Gln Cys Leu Thr Ile Pro Cys
140                 145                 150
```

(2) INFORMATION FOR SEQ ID NO:6:

(i) SEQUENCE CHARACTERISTICS:
        (A) LENGTH: 94 amino acids
        (B) TYPE: amino acid
        (D) TOPOLOGY: linear (ii) MOLECULE TYPE: protein (xi) SEQUENCE DESCRIPTION: SEQ ID NO:6:

```
Trp Tyr Phe Lys Gly Met Ser Arg Lys Glu Ala Glu Arg Gln Leu Leu
 1               5                   10                  15

Ser Pro Val Asn Lys Ser Gly Ala Phe Met Ile Arg Asp Ser Glu Thr
            20                  25                  30

Met Lys Gly Cys Phe Ser Leu Ser Val Arg Asp Ser Gly Asp Thr Val
        35                  40                  45

Lys His Tyr Lys Ile Arg Thr Leu Asp Asp Gly Gly Phe Phe Ile Ser
    50                  55                  60

Thr Arg Ile Pro Phe Pro Ser Leu Pro Glu Leu Val Arg His Tyr Gln
65                  70                  75                  80

Gly Lys Val Asp Gly Leu Cys Gln Cys Leu Thr Ile Pro Cys
                85                  90
```

(2) INFORMATION FOR SEQ ID NO:7:

(i) SEQUENCE CHARACTERISTICS:
        (A) LENGTH: 780 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 1..780

(xi) SEQUENCE DESCRIPTION: SEQ ID NO:7:

```
TGG GAG ATC CCG CGC GAG TCA CTG TCA CTG CAG AAG AAG CTT GGA GCT        48
Trp Glu Ile Pro Arg Glu Ser Leu Ser Leu Gln Lys Lys Leu Gly Ala
 95              100                 105                 110

GGA CAG TTT GGG GAT GTT TGG TTG GCC ATG TAC AAT GGA CAC ACA AAA        96
Gly Gln Phe Gly Asp Val Trp Leu Ala Met Tyr Asn Gly His Thr Lys
             115                 120                 125

GTA GCT GTA AAA ACA ATG AAG CCA GGC AGC ATG TCC CCC GGT GCC TTC       144
Val Ala Val Lys Thr Met Lys Pro Gly Ser Met Ser Pro Gly Ala Phe
         130                 135                 140

CTT GAA GAG GCA AAT CTG ATG AAG AGC TTG CAG CAT GAC CGG CTG GTG       192
Leu Glu Glu Ala Asn Leu Met Lys Ser Leu Gln His Asp Arg Leu Val
     145                 150                 155

CGG TTG CAT GCC GTT GTG ACT CAG GGG GAA CCA ATA TAT ATC ATT ACT       240
Arg Leu His Ala Val Val Thr Gln Gly Glu Pro Ile Tyr Ile Ile Thr
 160                 165                 170

GAG TAT ATG CAA AAG GGC AGT TTG CTG GAT TTC CTG AAA AGT GAA GAA       288
Glu Tyr Met Gln Lys Gly Ser Leu Leu Asp Phe Leu Lys Ser Glu Glu
175                 180                 185                 190

GGT AGC GAC CAA CCT CTG ATT CAA CTC ATT GAC TTC TCT GCC CAG ATT       336
Gly Ser Asp Gln Pro Leu Ile Gln Leu Ile Asp Phe Ser Ala Gln Ile
             195                 200                 205

GCA GAA GGA ATG TGG TTT ATT GAG CAA AGG AAT TAT ATT CAC CGT GAT       384
Ala Glu Gly Met Trp Phe Ile Glu Gln Arg Asn Tyr Ile His Arg Asp
         210                 215                 220

CTG AGG GCA GCA AAC TGC CTG GTA TCA GAA ACT TTG TTG TGC AAA ATA       432
Leu Arg Ala Ala Asn Cys Leu Val Ser Glu Thr Leu Leu Cys Lys Ile
     225                 230                 235

GCA GAC TTT GGG CTG GCC CGA GTG ATA GAG GAC AGC GAG TAT ACT GCC       480
Ala Asp Phe Gly Leu Ala Arg Val Ile Glu Asp Ser Glu Tyr Thr Ala
 240                 245                 250
```

```
AGG GAA GGT ACC AAA TTT CCC ATC AAG TGG ACA TCC CTG GAG GCT GCC    528
Arg Glu Gly Thr Lys Phe Pro Ile Lys Trp Thr Ser Leu Glu Ala Ala
255                 260                 265                 270

AAT TAT GGC TCT TTT ACT ATC AAG TCA GAT GTA TGG TCA TTT GGT GTA    576
Asn Tyr Gly Ser Phe Thr Ile Lys Ser Asp Val Trp Ser Phe Gly Val
                275                 280                 285

TTG CTA ACT GAA ATA ATA ACA TAT GGG AGG ACT CCA TAT CCA GGT ATG    624
Leu Leu Thr Glu Ile Ile Thr Tyr Gly Arg Thr Pro Tyr Pro Gly Met
            290                 295                 300

TCC AAC TCG GAG GTA ATT ACA GCC CTT GAG CGT GGT TAT CGC ATG CCG    672
Ser Asn Ser Glu Val Ile Thr Ala Leu Glu Arg Gly Tyr Arg Met Pro
        305                 310                 315

TGT CCC AGC ACT TGT CCA AAA GAG CTC TAC AGC ATC ATG CTC CAG TGT    720
Cys Pro Ser Thr Cys Pro Lys Glu Leu Tyr Ser Ile Met Leu Gln Cys
320                 325                 330

TGG CAG CAG GAC CCT GAG CAA CGG CCA ACG TTT GAA TAT TTA CAG AGC    768
Trp Gln Gln Asp Pro Glu Gln Arg Pro Thr Phe Glu Tyr Leu Gln Ser
335                 340                 345                 350

ATC CTA GAG GAC                                                    780
Ile Leu Glu Asp
```

(2) INFORMATION FOR SEQ ID NO:8:

(i) SEQUENCE CHARACTERISTICS:
        (A) LENGTH: 260 amino acids
        (B) TYPE: amino acid
        (D) TOPOLOGY: linear (ii) MOLECULE TYPE: protein (xi) SEQUENCE DESCRIPTION: SEQ ID NO:8:

```
Trp Glu Ile Pro Arg Glu Ser Leu Ser Leu Gln Lys Lys Leu Gly Ala
1               5                   10                  15

Gly Gln Phe Gly Asp Val Trp Leu Ala Met Tyr Asn Gly His Thr Lys
            20                  25                  30

Val Ala Val Lys Thr Met Lys Pro Gly Ser Met Ser Pro Gly Ala Phe
        35                  40                  45

Leu Glu Glu Ala Asn Leu Met Lys Ser Leu Gln His Asp Arg Leu Val
    50                  55                  60

Arg Leu His Ala Val Val Thr Gln Gly Glu Pro Ile Tyr Ile Ile Thr
65                  70                  75                  80

Glu Tyr Met Gln Lys Gly Ser Leu Leu Asp Phe Leu Lys Ser Glu Glu
                85                  90                  95

Gly Ser Asp Gln Pro Leu Ile Gln Leu Ile Asp Phe Ser Ala Gln Ile
            100                 105                 110

Ala Glu Gly Met Trp Phe Ile Glu Gln Arg Asn Tyr Ile His Arg Asp
        115                 120                 125

Leu Arg Ala Ala Asn Cys Leu Val Ser Glu Thr Leu Leu Cys Lys Ile
    130                 135                 140

Ala Asp Phe Gly Leu Ala Arg Val Ile Glu Asp Ser Glu Tyr Thr Ala
145                 150                 155                 160

Arg Glu Gly Thr Lys Phe Pro Ile Lys Trp Thr Ser Leu Glu Ala Ala
                165                 170                 175

Asn Tyr Gly Ser Phe Thr Ile Lys Ser Asp Val Trp Ser Phe Gly Val
            180                 185                 190

Leu Leu Thr Glu Ile Ile Thr Tyr Gly Arg Thr Pro Tyr Pro Gly Met
        195                 200                 205
```

```
Ser Asn Ser Glu Val Ile Thr Ala Leu Glu Arg Gly Tyr Arg Met Pro
    210             215                 220

Cys Pro Ser Thr Cys Pro Lys Glu Leu Tyr Ser Ile Met Leu Gln Cys
225             230                 235                 240

Trp Gln Gln Asp Pro Glu Gln Arg Pro Thr Phe Glu Tyr Leu Gln Ser
                245                 250                 255

Ile Leu Glu Asp
        260
```

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:9:

TGGCTCTGTA CTGTGATC                                                  18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:10:

GTCATACAAA GCCAGCAG                                                  18

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO:11:

GTAGAAACAA TGAAGCCAGG CAGC                                        24

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO

-continued (xi) SEQUENCE DESCRIPTION: SEQ ID NO:12:

TTAAGGTTGT GCCTGGAACT G                                                                 21

ANTIBODIES TO A NOVEL SRC-FAMILY KINASE

CROSS-REFERENCE TO RELATED APPLICATIONS

The present application is a non-provisional application claiming the priority of copending provisional U.S. Ser. No. 60/071,269 filed Jan. 13, 1998, the disclosure of which is hereby incorporated by reference in its entirety. Applicants claim the benefits of this application under 35 U.S.C. § 119(e).

FIELD OF THE INVENTION

The present invention pertains to a novel src-family kinase, its role in embryonic development and in carcinogenesis. Amino acid and nucleic acid sequences of the novel src family kinase are disclosed. Methods of using the novel src family kinase are also included.

BACKGROUND OF THE INVENTION

The src family of non-receptor tyrosine kinases are a well-studied class of signaling molecules which heretofore have not been shown to play any role in mesoderm induction. All src-family proteins contain catalytic, tyrosine kinase domains, as well as src-homology 2 and src-homology 3 (SH2 and SH3) domains. These domains were first discovered in cytoplasmic (non-receptor) protein tyrosine kinases such as the src oncogene product, thus leading to the term 'src homology domains' [Sadowski et al., *Mol Cell. Biol* 6:4396–4408 (1986)]. src is the prototypical member of this gene family, and was the first characterized proto-oncogene: elimination of a ncegative regulatory tyrosine at the carboxy-terminus of src converts the molecule to a potent transforming agent, and all members of the family share this residue [Brown and Cooper, *Biochimica el Biophysica Aclt,* 1287:121–149 (1996)]. Nine src-related genes have been cloned thus far, and several of these have been shown to be required for normal function of the immune and nervous systems [Brown and Cooper, *Biochimica et Biophysica Acta,* 1287:121–149 (1996)]. No definitive role, however, has been described for these proteins during early development. SH2 and SH3 domains are two individual protein modules that play an intermediary role in eukaryotic cellular signal transduction. After the initiation of the signal by the binding of an extracellular ligand to a transmembrane receptor having an associated tyrosine kinase, SH2 and SH3 domains mediate many of the protein-protein interactions that are necessary for transmission of the signal [Cantlcy el al., *Cell,* 64:281–302 (1991); Schlessinger el al., *Neuron,* 9:383–391 (1992); Pawson el al., *Curr. Biol.,* 3:434–442 (1993)].

The unique importance of these domains became clear with the discovery of the crk oncogene product, which consists of little more than an SH2 and an SH3 domain fused to the viral gag protein, but is capable of transforming cells [Mayer el al., *Nature,* 332:272–275 (1988)]. SH2 and SH3 domains have been identified in molecules with distinct functions that act downstream from the receptors for, among others, epidermal growth actor (EGF), platelet-derived growth factor (PDGF), insulin and interferon, and the T-cell receptor [Koch el al., *Science,* 252:668–674 (1991)].

The key aspect of the function of SH2 and SH3 domains is their ability to recognize particular amino acid sequences in their target proteins: SH2 domains bind tightly to phosphorylated tyrosine residues [Andeirson el al., *Science;* 250:979–982 (1990); Matsuda el al., *Science* 248:15537–1539 (1990); Moran el al., *Proc. Natl. Acad. Sci. USA* 87:8622–8626 (1990); Mayer el al., *Proc. Natl. Acad. Sci. USA,* 88:627–631 (1991); Songyang et al., *Cell* 72:767–778 (1993)] whereas SH3 domains bind to unmodified peptide sequence that are rich in proline and hydrophobic amino acids [Cicchetti et al., *Science* 257:803–806 (1992); Ren el al., *Science* 259:1157–1161 (1993)]. The modular nature of these domains is made clear by the fact that they occur in different positions in the polypeptide chains of the intact proteins of which they are a part, and that the binding functions can often be reproduced by isolated domains. As indicated above, however, the role of src-family tyrosine kinases in the signalling pathway during embryonic development has been obscure. During embryogenesis, inductive interactions among cells underlie the development of much of the body plan. The process of mesoderm formation is a critical and well-characterized example of an early inductive event. In *Xenopus laevis,* factors secreted from the vegetal pole induce mesoderm in the adjacent marginal zone [Klein and *Melton, Endocr. Rev.,* 15:326–341 (1994)]. During mesoderm induction, it is essential that information received by the marginal zone cells be communicated from the cell surface to the nucleus, where determination of cell fate is driven by an alteration in gene expression. Members of both the Transforming Growth Factor-b (TGF-b) and Fibroblast Growth Factor (FGF) ligand families appear to play essential roles in the formation of mesoderm [Klein and *Melton, Endocr. Rev,* 15:326–341 (1994)]. The downstream effectors of these growth factors are distinct: TGF-b ligands signal through serine-threonine kinase receptors, whose effects are mediated through the recently characterized Smad proteins [Massague et al, *TICB,* 7:187–192 (1997)]. The Smad pathway appears to be quite direct: although a number of positively and negatively acting Smads may interact in mesoderm induction, few other factors seem to be involved in the propagation of signal from cell surface to nucleus. Signaling through the FGF receptor tyrosine kinase, however, appears to be significantly more complex, involving a multiprotein interaction at the plasma membrane, and subsequent activation of the ras/MAP kinase pathway [Labonne and Whitman, *Dev. Biol.,* 183:9–20 (1997), and references therein).

The importance of isolating and identifying the factors involved in early development cannot be emphasized. For example, screening for mutations of such factors, in utero, can serve as a powerful tool in early identification of developmental defects. Therefore, there is a need to isolate and identify factors that mediate the signaling initiated at the FGF receptor. Furthermore, there is need to obtain nucleic acid probes and antibodies which can be used to identify the absence of such factors and/or defects in such factors.

The citation of any reference herein should not be construed as an admission that such reference is available as "Prior Art" to the instant application.

SUMMARY OF THE INVENTION

The present invention provides a unique src-family kinase (SFK) that plays a role in the transformation of uncommitted embryonic cells to mesodermal cells. Furthermore, this src-family kinase (also denoted as *laloo*) has properties that are consistent with it being a proto-oncogene.

One aspect of the invention provides an isolated nucleic acid encoding a src-family kinase comprising an amino acid sequence substantially homologous to that of SEQ ID NO:2, and having the following structural/functional domains: (i) a catalytic tyrosine kinase domain; (ii) a src-homology-2 (SH2) domain; and (iii) a src-homology-3 (SF13) domain. In a particular embodiment, the isolated nucleic acid encodes a src-family kinase that further comprises a tyrosine in the carboxyl-terminal portion of the protein which can act as a site of negative regulation. In a preferred embodiment the nucleic acid encodes a vertebrate SFK. In one particular embodiment of this type the nucleic acid encodes a human SFK, (*human laloo*).

In a more particular embodiment the isolated nucleic acid encodes a vertebrate src-family kinase (SFEK) comprising the amino acid sequence of SEQ ID NO:2. In another particular embodiment the isolated nucleic acid encodes a vertebrate SFK comprising the amino acid sequence of SEQ ID NO:2 with a conservative amino acid substitution. In a preferred embodiment of the present invention, the isolated nucleic acid encodes a *Xenopus laloo* and comprises the coding sequence of SEQ ID NO: 1.

In an alternative embodiment of this type the isolated nucleic acid contains a nonconservative amino acid substitution which alters a functional or regulatory property of the SFK. In one particular embodiment of this type, the tyrosine at position 492 in SEQ ID NO:2 is replaced with a pheniylalanine (Y492F). This tyrosine is a phosphorylatable site that is involved in the regulation of the SFK. In another such embodiment the arginine at position 259 in SFQ ID NO:2 is replaced with a glutamic acid (K259E). This arginine is contained in the catalytic site of the SFK. These modifications are only meant as examples, and analogous substitutions in either SEQ ID NO:2, or SEQ ID NO:2 having a conservative amino acid substitution are fully contemplated by the present invention.

The present invention also provides oligonucleotide primers and probes capable of screening for the nucleic acids of the present invention. In a preferred embodiment of this type the primer or probe has specificity for a nucleic acid encoding an SFK having the amino acid sequence of SEQ ID NO:2 or SEQ ID NO:2 having a conservative amino acid substitution. In a more preferred embodiment of the present invention, the primer or probe has specificity for a nucleic acid encoding a *Xenopus laloo* comprising the coding sequence of SEQ ID NO:1. In an embodiment of this type, the primer or probe has a nucleotide sequence of 15 to 48, (preferably 24 to 36 nucleotides) that is identical to a sequence contained in SEQ ID NO:1.

The isolated nucleic acids of the present invention can further comprise a heterologous nucleotide sequence. In one particular embodiment of this type the nucleic acid encoding an SFK having the amino acid sequence of SEQ ID NO:2 further comprises a heterologous nucleotide sequence. In another particular embodiment, the nucleic acid encoding an SFK having the amino acid sequence of SEQ ID NO:2 having a conservative amino acid substitution further comprises a heterologous nucleotide sequence. In still another embodiment an isolated nucleic acid encoding a SFK but containing a nonconservative amino acid substitution which alters the functional properties of the SFK further comprises a heterologous nucleotide sequence.

Another aspect of the present invention includes nucleic acids that encode fragments of the SFKs of the present invention. In one such embodiment the isolated nucleic acid comprises a nucleotide sequence encoding a src-homology-3 (SH3) domain of a vertebrate src-family kinase (SFK) that has the amino acid sequence of SEQ ID NO:4 with a conservative amino acid substitution. In a related embodiment the nucleic acid encodes a SH3 domain of a SFK that has the amino acid sequence of SEQ ID NO:4.

In a more particular embodiment the isolated nucleic acid comprises the coding sequence of SEQ ID NO:3. Any of these nucleic acids can further comprise a heterologous nucleotide sequence.

In another such embodiment the isolated nucleic acid comprises a nucleotide sequence encoding a src-homology-2 (SH2) domain of a vertebrate src-family kinase (SFK) that has the amino acid sequence of SEQ ID NO:6 with a conservative amino acid substitution. In a related embodiment the nucleic acid encodes a SH2 domain of a SFK that has the amino acid sequence of SEQ ID NO:6. In a more particular embodiment the isolated nucleic acid comprises the coding sequence of SEQ ID NO:5. Any of these nucleic acids can further comprise a heterologous nucleotide sequence.

In another such embodiment the isolated nucleic acid comprises a nucleotide sequence encoding a catalytic tyrosine kinase domain of a vertebrate src-family kinase (SFK) that has the amino acid sequence of SFEQ ID NO:8 with a conservative amino acid substitution. In a related embodiment the nucleic acid encodes a catalytic tyrosine kinase domain of a SFK that has the amino acid sequence of SFQ ID NO:8. In a more particular embodiment the isolated nucleic acid comprises the coding sequence of SEQ ID NO:7. Any of these nucleic acids can further comprise a heterologous nucleotide sequence.

Any of the isolated nucleic acids of the present invention can be operatively linked to an expression control sequence. The present invention further provides a unicellular host transformed or transfected with one of the nucleic acids operatively linked to an expression control sequence. In addition the present invention provides a method of expressing a SFK, or fragment thereof, encoded by this nucleic acid comprising culturing the unicellular host in an appropriate cell culture medium under conditions that provide for expression of the SFK or fragment thereof, by the cell. In one particular embodiment of this type, the present invention provides a method further comprising the step of purifying the SFK or fragment thereof. The purified form of the SINK, or fragment thereof, obtained by this method is also part of the present invention.

The present invention also provides recombinant viruses transformed with a nucleic acid of the present invention. In one particular embodiment of this type, the transformed recombinant virus is used in a gene therapy protocol for correcting an error or deficiency of *laloo*. In an alternative embodiment, the transformed recombinant virus is used to further probe the role of *laloo* in cell.

In still another aspect the present invention provides an isolated vertebrate src-family kinase (SFK) having an amino acid sequence substantially homologous to that of SEQ ID NO:2, comprising the following structural/functional domains (i) a catalytic tyrosine kinase domain; (ii) a src-homology-2 domain; and (iii) a src-homology-3 domain. In a particular embodiment, the src-family kinase further comprises a tyrosine in the carboxyl-terminal portion of the protein which can act as a site of negative regulation. In a preferred embodiment the SFK is a vertebrate protein. In one particular embodiment of this type the SFK is the human protein (*human laloo*).

In a more particular embodiment the vertebrate src-family kinase (SFK) comprises the amino acid sequence of SEQ ID NO:2. In another particular embodiment the vertebrate SFK comprises the amino acid sequence of SEQ ID NO:2 with a conservative amino acid substitution.

In an alternative embodiment of this type the SFK contains a nonconservative amino acid substitution which alters the functional properties of the SFK. In one particular embodiment of this type, the tyrosine at position 492 in SEQ ID NO:2 is replaced with a phenylalanine (Y492F). In another such embodiment the arginine at position 259 in SEQ ID NO:2 is replaced with a glutamic acid (K259E). These modifications are only meant as examples, and analogous substitutions in either SEQ ID NO:2, or SEQ ID NO:2 having a conservative amino acid substitution are fully contemplated by the present invention. In addition, the present invention also includes proteolytic fragments of the isolated SFKs of the present invention. In a preferred embodiment of this type, the proteolytic fragment is derived from the proteolytic cleavage of SEQ II) NO:2.

The present invention also provides fusion proteins comprising an heterologous amino acid sequence and an SFK or fragment thereof. In one such embodiment the SFK or fragment thereof, comprises SEQ ID NO:2. In another such embodiment the SFK or fragment thereof, comprises SEQ ID NO:2 with a conservative amino acid substitution. In still another such embodiment the SFK or fragment thereof, comprises SEQ ID NO:4. In yet another such embodiment the SFK or fragment thereof, comprises SFQ ID NO:4 with a conservative amino acid substitution. In still another such embodiment the SFK or fragment thereof, comprises SEQ ID NO:6. In another such embodiment the SFK or fragment thereof, comprises SEQ ID NO:6 with a conservative amino acid substitution. In still another such embodiment the SFK or fragment thereof, comprises SEQ ID NO:8. In yet another such embodiment the SFK or fragment thereof, comprises SEQ ID NO:8 with a conservative amino acid substitution. In one particular embodiment the heterologous amino acid sequence is the amino acid sequence of green fluorescent protein.

The present invention also provides antibodies to all of the SFKs and fragments thereof, of the present invention. In a preferred embodiment the antibody is to a xenopus src-family kinase (SFK) having the amino acid sequence of SEQ ID NO:2. In one such embodiment the antibody is a polyclonal antibody. In another embodiment the antibody is a monoclonal antibody. In a preferred embodiment the monoclonal antibody is a chimeric antibody. The present invention also includes immortal cell lines that produce a monoclonal antibody of the present invention.

The present invention further provides methods of identifying potential drugs that modulate the ability of the SFKs of the present invention to induce the transcription of mesodermal markers. One such embodiment comprises the step of administering an SFK into an animal pole of an embryo in the presence of an agent (e.g., a potential drug). An animal pole explant is isolated from the embryo and subsequently cultured. The RNA of the animal pole is extracted and the transcription of a mesodermal marker protein is assayed. The amount of transcription of the mesodermal marker protein is then compared with that determined in a control procedure in which the agent was not included. An agent that enhances or diminishes the transcription of the mesodermal marker protein (relative to the control) is identified as a potential drug that modulates the ability of the SFK to induce the transcription of mesodermal markers.

In one particular embodiment the administering of the SFK is performed by injecting an mRNA encoding the SFK into the embryo. In a preferred embodiment the embryo is a 2-cell stage embryo. In a more preferred embodiment the 2-cell stage embryo is a xenopus embryo. In another preferred embodiment, the isolated animal pole explant is isolated at the late blastula stage. In a preferred embodiment of this type, the animal pole explant is cultured until the midgastrula or late neurula stagyes.

In one embodiment the mesodermal marker is Xbra. In another embodiment the mesodermal marker is Xwnt8. In yet another embodiment the mesodermal marker is HoxB9. In still another embodiment the mesodermal marker is muscle actin.

Preferably, the assaying of the transcription of the mesodermal marker protein is performed with reverse transcriptase polymerase chain reaction (RT-PCR). Alternatively, the mesodermal marker transcript can be translated and identified with an antibody. The present invention also envisions mesodermal marker proteins that are fusion or chimeric proteins which can be identified by their heterologous amino acid sequence, e.g., a FLAG-tag or green fluorescent protein.

Accordingly, it is a principal object of the present invention to provide a purified src-family kinase, *laloo,* which functions in the early development of vertebrate embryos.

It is a further object of the present invention to provide the amino acid and nucleic acid sequences of *Xenopus laloo.*

It is a further object of the present invention to identify a potential oncogene.

It is a further object of the present invention to provide an antibody that is specific for *laloo.*

It is a further object of the present invention to provide a method of diagnosing subjects having a pre-cancerous condition related to a mutated *laloo.*

It is a further object of the present invention to provide a method of diagnosing an early developmental defect in order to prevent birth defects.

It is a further object of the present invention to provide a method of screening drugs to identify a drug that either enhances or diminishes the activity of *laloo.*

These and other aspects of the present invention will be better appreciated by reference to the following drawings and Detailed Description.

BRIEF DESCRIPTION OF THE DRAWINGS

FIGS. 1A–D shows the isolation of *laloo,* a src-family kinase.

FIGS. 1A and 1B show that the overexpression of *laloo* induces ectopic tail-like structures.

FIG. 1A depicts the control embryo, stage 35, lateral view, anterior is to left.

FIG. 1B depicts the dorsal view of three embryos, stage 35, each injected with 1 ng of gastrula library pool 27AIJA (*laloo*).

FIG. 1C is the nucleotide sequence (SEQ ID NO:1) and conceptual translation of *laloo* (SEQ ID NO:2). Residues mutated in this study (K259, Y492) are boxed.

FIG. 1C shows the phylogenetic tree of selected vertebrate src-family kinases. The full-length protein sequences of *Xenopus laloo,* the nine previously characterized src-family genes and the related csk from a number of vertebrate species were compared using the Clustal program in the DNA Star software package. Protein sequences are named according to species of origin (h, human; m, mouse; r, rat; c, chicken; x, frog). Sequence ID numbers: hSrc, 125711; cSrc, 125710; xSrc1, 125703; xSrc2, 125705; hYes, 125870; cYes, 125869; xYcs, 125871; hFyn, 125370; mFyn, 729896; cFyn, 462444; xFyn, 125371; cYrk, 462471; hFgr, 125358; mFgr, 125359; hLyn, 125480; hLynB , 2117805; rLyn, 2507209; mLyn, 2707208; xLyn, 2114076; hhck, 1170188;

rHck, 1708153; mlhck, 1170189; hlck, 125474; mLck, 125475; cLck, 1170731; hBlk, 1705485; mBlk, 125243; hCsk, 729887; rCsk, 417209; mCsk, 729888; cCsk, 729886.

Figure 2A:
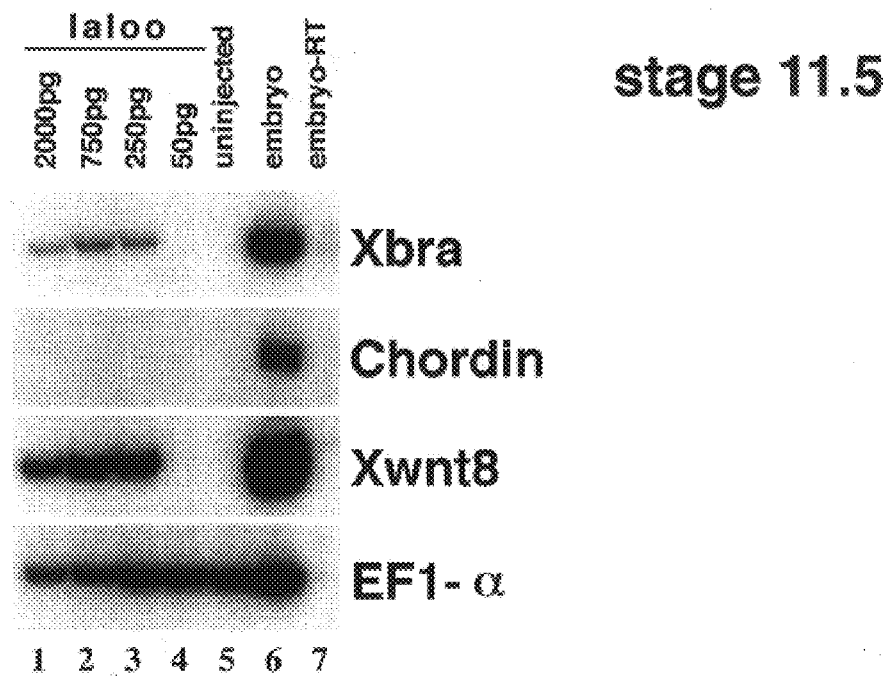
Figure 2B:
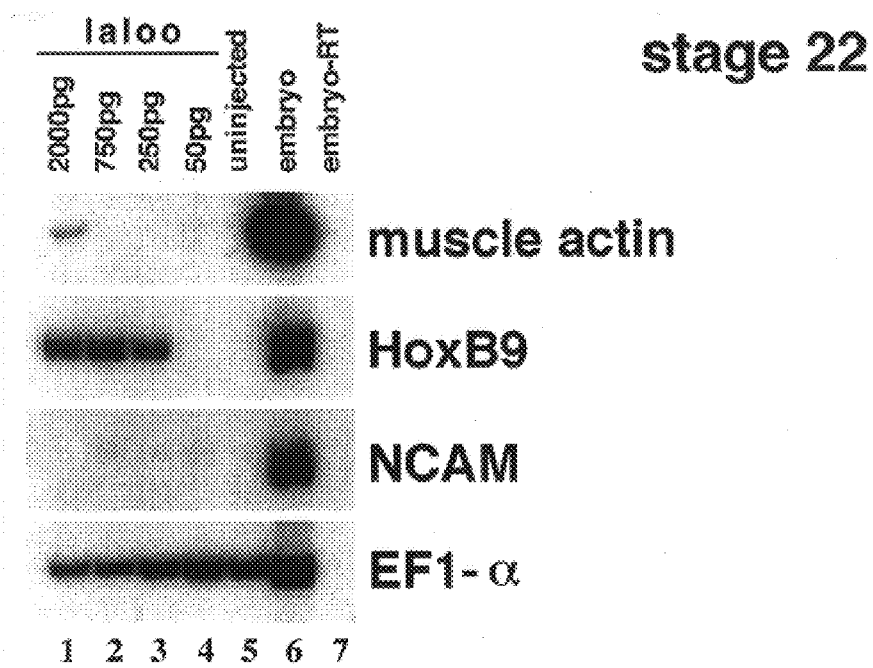

FIGS. 2A–B shows that ectopic *laloo* induces mesoderm in ectodermal explants. Synthetic *laloo* RNA, as listed, was injected into both blastomeres of 2-cell stage embryos. Animal caps were dissected at late blastula stages (stage 9) and cultured in saline until the stages listed, at which point RT-PCR analysis was performed. EF1-a is used as a loading control. The "-RT" lane contains all reagents except reverse transcriptase and was used as a negative control.

FIG. 2A shows the RT-PCR analysis of animal caps cultured until midgastrula stages (stage 11.5). Xbra is a marker of both notochord and of all non-involuted mesoderm at this stage. Chordin is a marker of dorsal mesoderm, and Xwnt8 is a marker of ventrolateral mesoderm.

FIG. 2B shows the RT-PCR analysis of animal caps cultured until late neurula stages (stage 22). Muscle actin is a marker of mediolateral mesoderm. HoxB9 is expressed in both the spinal cord and mediolateral mesoderm at this stage. NCAM is a pan-neural marker.

Figure 3:
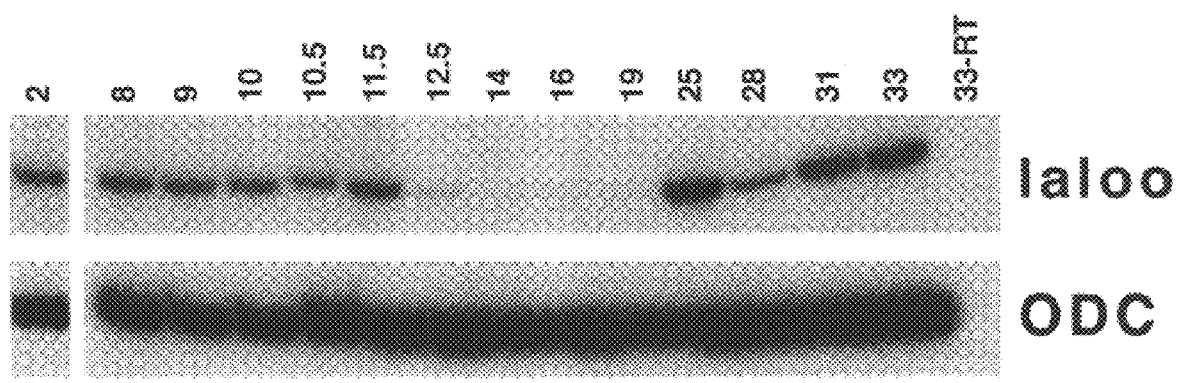

FIG. 3 shows the temporal expression of *laloo*. FIG. 3 shows the RT-PCR analysis of *laloo* expression during development. ODC is used as a loading control. The "-RT" lane contains all reagents except reverse transcriptase and was used as a negative control.

Figure 4:
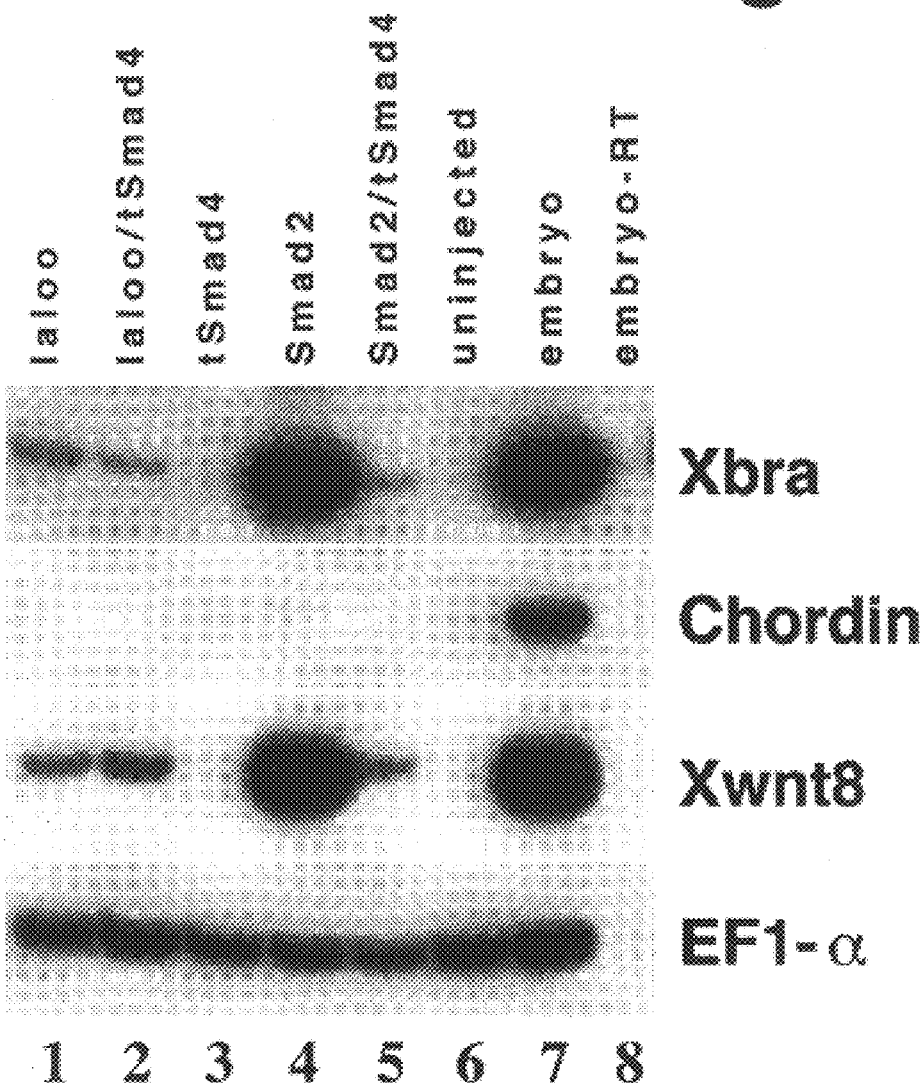

FIG. 4 shows that the induction of mesoderm by *laloo* is unaffected by inhibition of Smad1 and Smad2. Co-injection of dominant inhibitory Smad4 (tSmad4) fails to block *laloo*-mediated mesodermal induction. Synthetic RNA, as listed, was injected into both blastomeres of 2-cell stage embryos. Animal caps were dissected at late blastula stages and cultured until midgastrula stages. Controls and molecular markers are as listed in FIG. 2. In the experiment shown here, 750 pg each of *laloo*, Smad2, and tSmad4 were injected, as listed.

Figure 5A:
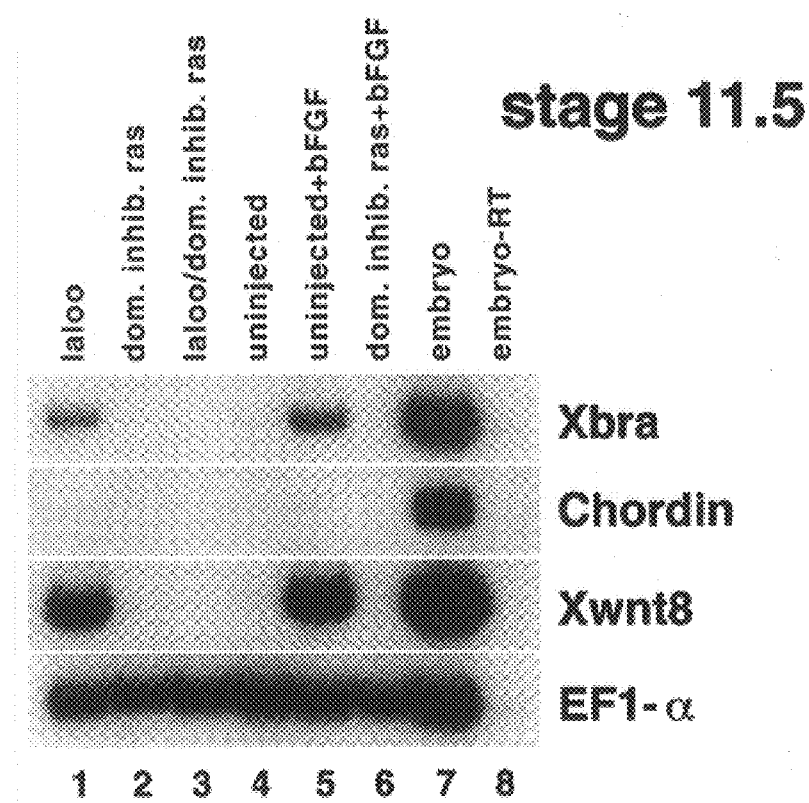
Figure 5B:
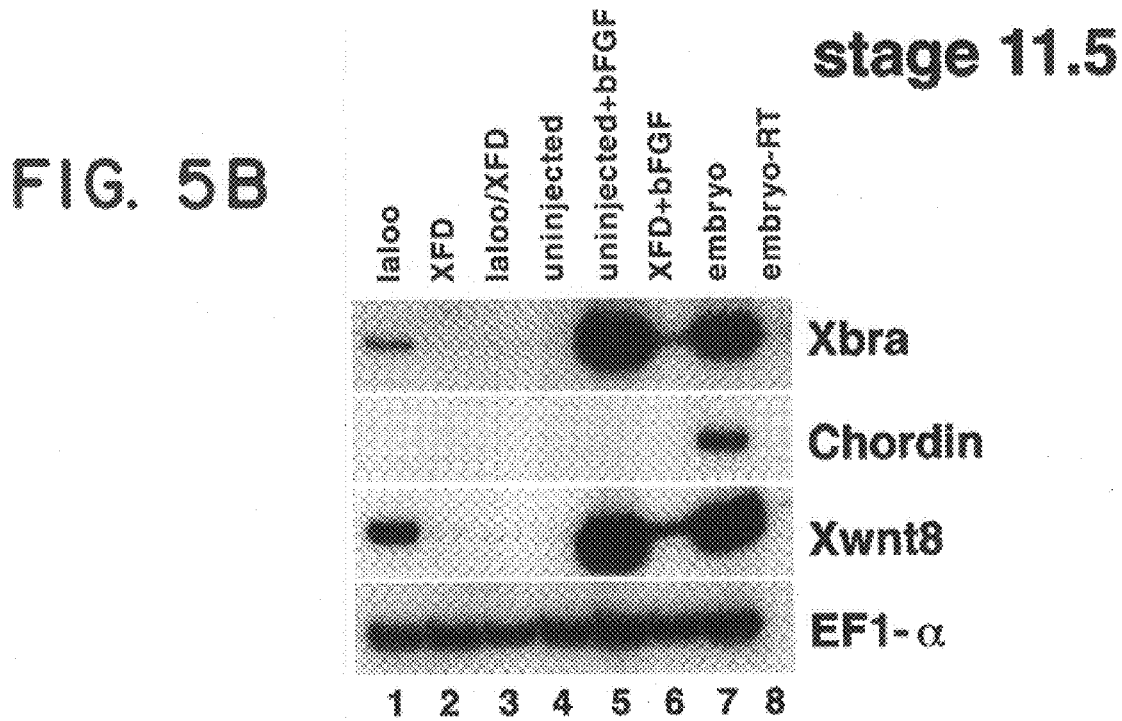

FIGS. 5A–B shows that the inhibition of the FGF signaling pathway blocks induction of mesoderm by *laloo*. Synthetic RNA, as listed, was injected into both blastomeres of 2-cell stage embryos. Animal caps were dissected at late blastula stages and cultured until midgastrula stages.

FIG. 5A shows that dominant-inhibitory ras (dom. inhib. ras) blocks induction of both Xbra and Xwnt8 by *laloo*. In the experiment shown here, 500 pg of *laloo*, and 1.0 ng of dominant inhibitory RNA were injected, as listed.

FIG. 5B shows that a dominant inhibitory, truncated FGF receptor (XFD) blocks induction of both Xbra and Xwnt8 by *laloo*. Controls and molecular markers are as listed in FIG. 2. In the experiment shown here, 750 pg of *laloo*, and 1.5 ng of XFD RNA were injected, as listed. bFGF was added to a final concentration of 75 ng/ml.

Figure 6A:
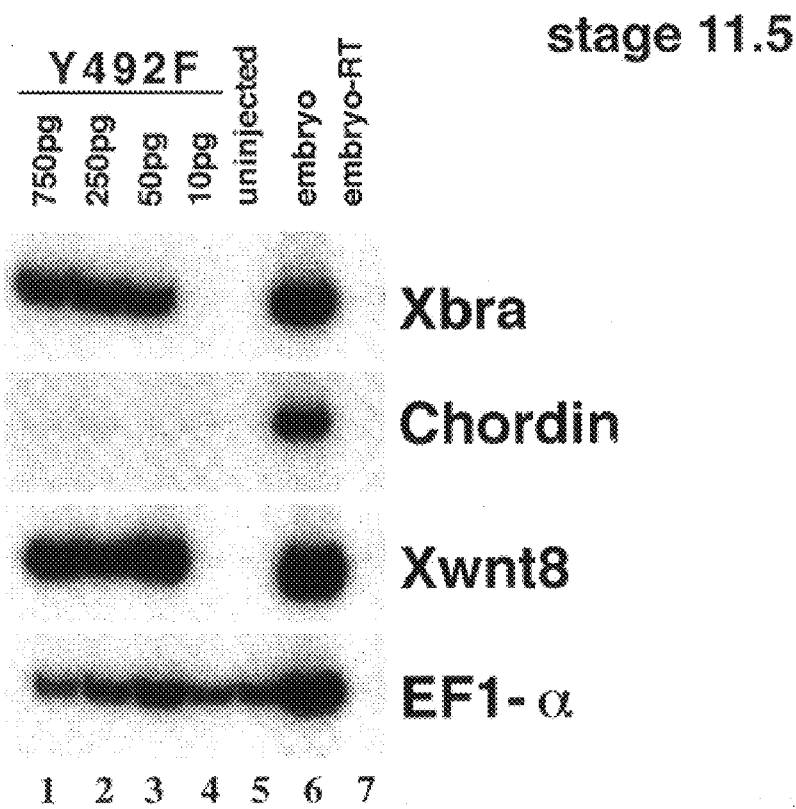
Figure 6B:
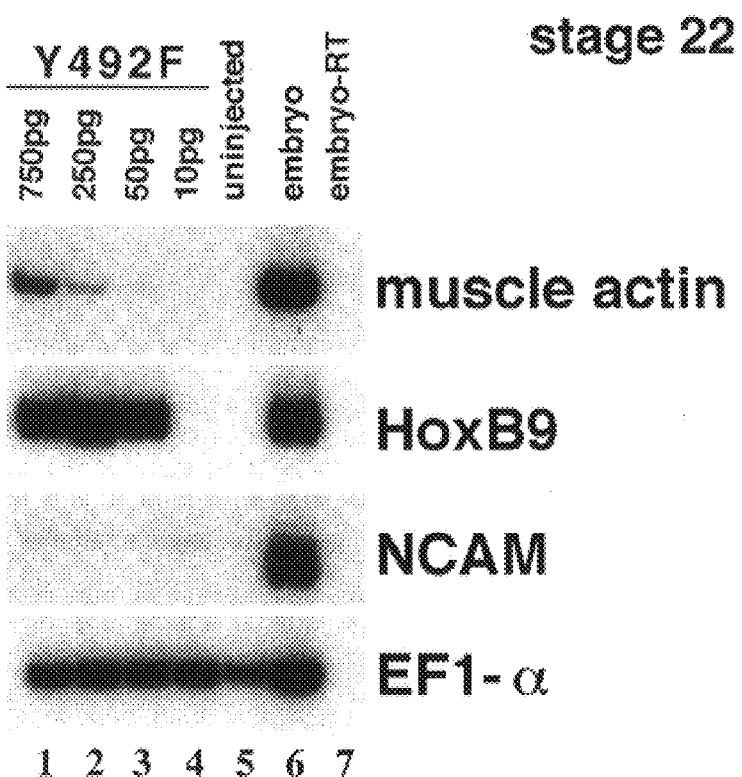

FIGS. 6A–B shows that a C-terminal tyrosine residue acts to negatively regulate *laloo* activity. A *laloo* point mutant was constructed, in which tyrosine 492 was mutated to a phenylalaniine (Y492F). Y492F is a more potent mesodermal inducer than wild-type *laloo*. RNA from this construct was injected into both blastorneres of 2-cell stage embryos. Animal caps were dissected at late blastula stages and cultured until midgastrula (FIG. 6A) or late neurula (FIG. 6B) stages. Controls and molecular markers are as listed in FIGS. 2A–B.

FIG. 7 shows that a hyperactive *laloo* mutant bypasses inhibition by the truncated FGF receptor. Synthetic RNA, as listed, was injected into both blastomeres of 2-cell stage embryos. Animal caps were dissected at late blastula stages and cultured until midgastrula stages. Dominant-inhibitory ras (dom. inhib. ras) blocks mesoderm induction by both wild-type *laloo* and the point mutant Y492F. The truncated FGF receptor (XFD) also blocks mesoderm induction by *laloo*, but does not block induction by Y492F. In the experiment shown here, 750 pg of *laloo*, 250 pg of Y492F, 1.0 ng of doin. inhib. ras, and 1.5 ng of XFD were injected, as listed. bFGF was added to a final concentration of 25 ng/ml.

Figure 8A:
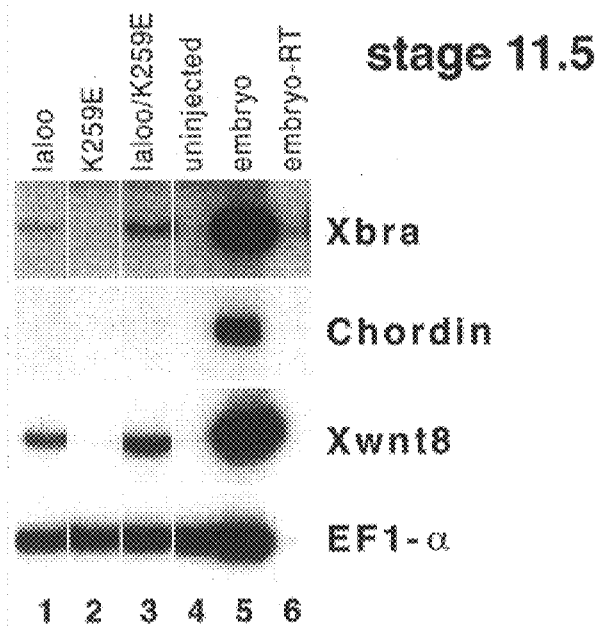
Figure 8B:
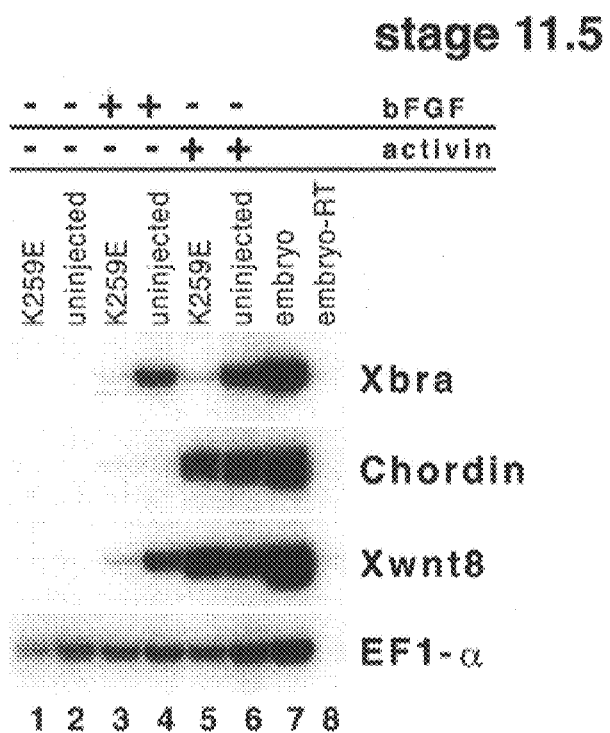

FIGS. 8A–B shows that a kinase-defective *laloo* mutant does not induce mesoderm, and inhibits the activity of mesoderm-inducing growth factors. A *laloo* point mutant was constructed, in which lysine 259 was mutated to glutamic acid (K259E). Synthetic RNA, as listed, was injected into both blastomeres of 2-cell stage embryos. Animal caps were dissected at late blastula stages and cultured until midgastrula stages. Controls and molecular markers are as listed in FIG. 2.

FIG. 8A shows the induction of mesoderm by *laloo* is mediated through the *laloo* kinase domain. K259E does not induce the mesodermal markers Xbra or Xwnt8, nor does it block mesoderm induction by wild-type *laloo*. In the experiment shown here, 800 pg of *laloo*, and 1.6 ng of K259E RNA were injected, as listed.

FIG. 8B shows that K259E inhibits mesoderm induction by bFGF and activin. Animal caps injected with K259E RNA were cultured in the presence of either bFGF or activin protein. Pre-injection of K259E RNA inhibits the FGF-mediated induction of the mesodermal markers Xbra or Xwnt8, as well as the induction of Xbra by activin. Activin-mediated induction of Xwnt8 and chordini are unaffected by K259E expression. In the experiment shown here, 2 ng of K259E RNA was injected, as listed. bFGF was added to a final concentration of 25 ng/ml. For activin, 2 ul of activin RNA-injected oocyte supernatant was used per ml.

DETAILED DESCRIPTION OF THE INVENTION

The present invention discloses an isolated member of the src family of non-receptor tyrosine kinases (SFK). The SFK of the present invention also named *laloo* induces mesoderm in competent ectoderm. This induction requires a functional kinase domain. Mesoderm induction by *laloo* can be blocked by both dominant inhibitory ras and the dominant inhibitory FGI, receptor (XFD). Inhibition by XFD, but not by dominant inhibitory ras, is overcome by the hyperactive *laloo* point mutant Y492F (see SEQ ID NO:2). Overexpression of a kinase-defective *laloo* mutant blocks induction of some mesodermal markers by both bFGF and activin protein, indicating that *laloo* is a necessary component of endogenous mesoderm induction.

The present invention further discloses that a src-related kinase can induce mesoderm. Dominant inhibitory ras completely blocks mesoderm induction by *laloo*. consistent with the observation that other src-family kinases transmit signals through ras [Brown and Cooper, *Biochimica et Biophysica Acta*, 1287:121–149 (1996)]. The molecular interactions proposed to link src-family kinases to ras are several, and may include phosphorylation of she and/or rasGAP [Rozakis-Adcock et al, *Nature*, 360:689–692 (1992); Ellis et al, *Nature*, 343:377–381 (1990)]. In addition, XFD blocks induction by *laloo*, but has no effect on the *laloo* mutant Y492F. These results indicate that the mesoderm-inducing activity of ectopic *laloo* is dependent upon a basal level of signaling through the FGF receptor, and that this requirement is mediated through tyrosine 492 of *laloo* (SEQ ID NO:2). The present invention also discloses that overexpression of a kinase-defective *laloo* point mutant (K259FE) blocks mesoderm induction by BFGF.

The present invention therefore demonstrates that the co-injection of either dominant-inhibitory ras or a truncated FGF receptor (XFD) blocks the induction of mesoderm by *laloo,* that inhibition of XFD is bypassed by the Y492F mutation, and that overexperssion of non-functional *laloo* blocks mesoderm induction by bFGF. Although the present invention is not based on any particular mechanism or theory, one interpretation of these results places *laloo* as a required intermediate in the FlGF pathway, downstream of the FTF receptor and a putative phosphatase, and upstream of ras.

The present invention therefore discloses a gene and its corresponding gene product that are required during early embryonic development. Indeed, blocking the SFK of the present invention prevents normal embryonic development. This indicates that mutations in *human laloo,* for example, are likely to lead to birth defects. Accordingly, methods of screening for mutations of *laloo,* in utero, using primers or probes, that are readily obtainable from the teachings herein, are included in the present invention.

Furthermore, by analogy with other members of this gene family, the mutated and overexpressed *laloo* is almost certainly oncogenic. Therefore, methods of screening for mutations in *laloo* in post-natal subjects are also included in the present invention.

The teachings of the present invention can be used to readily isolate mammalian *laloos,* including *human laloo.* In addition, cross-reacting antibodies and oligonucleotide probes/primers can be used to identify potential abnormalities of cellular function/regulation. The nucleic acids and proteins (including antibodies) of the present invention can also be used in the elucidation of important regulatory pathways in Xenopus which are known to have striking analogies in mammals (including humans). Furthermore, drug screens, as exemplified herein, can be readily designed to identify agents which modify the action of *laloo* and/or naturally occuring abnormal *laloos.*
Nucleic Acids Peptides and Proteins In accordance with the present invention there may be employed conventional molecular biology, microbiology, and recombinant DNA techniques within the skill of the art. Such techniques are explained fully in the literature. See, e.g. Sambrook, Fritsch & Maniatis, *Molecular Cloning: A Laboratory Manual,* Second Edition (1989) Cold Spring Harbor laboratory Press, Cold Spring Harbor, New York (herein "Sambrook el al., 1989"); *DNA Cloning: A Practical Approach,* Volumes I and II (D. N. Glover ed. 1985); *Oligonucleolide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRI, Press, (1986)]; B. Perbal, *A Practical Guide, To Molecular Cloning* (1984); F. M. Auisubel el al. (eds.), *Current Protocols in Molecular Biology,* John Wiley & Sons, Inc. (1994).

Therefore, if appearing herein, the following, terms shall have the definitions set out below.

The terms "src-family kinase", "SFK", and "latoo" and any variants not specifically listed, may be used herein interchangeably, and as used throughout the present application and claims refer to proteinaceous material including single or multiple proteins, including a dimeric or larger form of the protein and extends to those proteins having the amino acid sequences described herein, and the profile of activities set forth herein. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the protein. Also, the terms "*laloo*" and "SFK" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of the peptide is retained.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adeninie, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter cilia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, CDNA from eukaryotic mRNA, genomic DNA sequences from cukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATIA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "Linder the control" of transcriptional and translational control sequences in a cell when RNA polymerase transcribes the coding sequence into mRNA. which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media! and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of about 15 or more nucleotides, preferably more than about 24 and more preferably about 36 nucleotides. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

Mutations can be made in nucleotide sequences of the present invention such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such conservative amino acid changes define the term "a conservative amino acid substitution" as used herein, which is used to denote one or more conservative changes.

A conservative change generally leads to less change in the structure and function of the resulting protein. A non-conservative change is more likely to alter the structure, activity or function of the resulting protein. The present invention should be considered to include all sequences encoding or containing one or more conservative amino acid substitutions which do not significantly alter the activity or binding characteristics of the resulting protein.

The following is one example of various (groupings of amino acids:

Amino Acids with Nonpolar R Groups
  Alanine; Valine; Leucine; Isoleucinie; Prolinie; Phenylalanine; Tryptophan; and Methionine.
Amino Acids with Uncharged Polar R Groups
  Glycine; Serine; Threonine; Cysteine; Tyrosine; Asparagine; and Glutamine.
Amino Acids with Charged Polar R Groups (Negatively Charged at Ph 6.0)
  Aspartic acid and Glutamic acid.
Basic Amino Acids (Positively Charged at pH 6.0)
  Lysine; Arginine; and Ilistidine (at pH 6.0)
  Particularly preferred conservative substitutions are:
  Lys for Arg and vice versa such that a positive charge may be maintained;
  Glu for Asp and vice versa such that a negative charge may be maintained;
  Ser for Thr such that a free —OH can be maintained; and
  Gln for Asn such that a free $NH_2$ can be maintained.

Amino acid substitutions may also be introduced to substitute an amino acid with a particularly preferable property. For example, a Cys may be introduced to create a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

A "heterologous amino acid sequence", as used herein is an amino acid sequence that is the part of a chimeric (or fusion) protein (or peptide) that comprises an SFK of the present invention or a fragment thereof which is not part of the naturally occuring SFK. The heterologous amino acid sequence can have a regulatory and/or structural property. In one such embodiment, the heterologous amino acid sequence contains a protein (e.g., green fluorescent protein) or peptide (e.g., FLAG) that functions as a means of detecting the chimeric/fusion protein/peptide.

A "heterologous nucleotide sequence" as used herein is a nucleotide sequence that is added to a nucleotide sequence of a SFK of the present invention or fragment thereof by recombinant methods to form a nucleic acid which is not naturally formed in nature. Such nucleic acids can encode an SFK protein of the present invention or fragment thereof, and an "heterologous amino acid sequence" forming a chimeric and/or fusion protein. Such heterolooous nucleotide sequences can also comprise non-coding sequences including restriction sites, regulatory sites, promoters and the like. Alternatively, a heterologous nucleotide sequence can contain a non-coding nucleotide sequence which serves as a specific oligonucleotide marker or has a functional property such a regulatory sequence, e.g., an iron responsive element (IRE), [Theil, *J. Biol. Chem.* 265:4771–4774 (1990); Theil el al., *Biofactors,* 4:8–93 (1993); Klausner et al., *Cell,* 72:19–28 (1993)].

A "heterol oous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologouls coding sequence is a construct where the coding sequence itself is not found in nature (e.g., a CDNA where the genomic coding sequence contains introns, or synthetic sequences having codons different than the native gene). Allelic variations or naturally-occurring mutational events do not give rise to a heterologous region of DNA as defined herein.

"Heterologous DNA" refers to DNA not naturally located in the cell, or in a chromosomal site of the cell. Preferably, the heterologous DNA includes a gene foreign to the cell.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforminig DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

As used herein, the terms "restriction endoniucleases" and "restriction enzymes" refer to bacterial enzymes, each of which cut double-stranded DNA at or near a specific nucleotide sequence.

Two DNA sequences are "substantially homologous" when at least about 80% (preferably at least about 90%, and most preferably at least about 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning. Vols. I & II, supra; Nucleic Acid Hybridization, supra. Likewise, two polypeptide sequences arc "substantially homologous" when at least about 80% (preferably at least about 90%. and most preferably at least about 95%) of the amino acids are either identical or contain conservative changes, as defined above, over the defined length of the polypeptide sequences. Preferably, the similar or homologous sequences are identified by alignment using, e.g., the GCG pileup program (Genetics Computer Group, Program Manual for the GCG Package, Version 7, Madison Wis.), using the default parameters.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook el al., supra). The conditions of temperature and ionic strength determine the "stringency" of the hybridization. For preliminary screening for homologous nucleic acids, low stringency hybridization conditions are used corresponding to 50° C. as described by Church and Gilbert [*Proc. Natl. Acad. Sci. USA,* 81:1991–1995 (1984).] Washes are performed in 2×SSC/0.1% SDS at 50° C. Moderate stringency hybridization conditions correspond to a higher temperature e.g., 60° C. High stringency hybridization conditions are performed at 65° C. Washes in this case are performed in 0.3×SSC/0.1% SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook el al., supra, 9.50–0.51). For hybridization with shorter nucleic acids, i.e., oligonucleotides, the position of mismatches becomes more important, and the length of the oliglonucleotide determines its specificity (see Sambrook el al., supra, 11.7–11.8). Preferably a minimum length for a hybridizable nucleic acid is at least about 12 nucleotides; preferably at least about 18 nucleotides; and more preferably the length is at least about 27 nucleotides; and most preferably 36 nucleotides or more. In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$, is 65° C.

The term "standard hybridization conditions" refers to salt and temperature conditions substantially equivalent to 5×SSC and 65° C. for both hybridization and wash.

The term "approximately" is used interchangeably with the term "about" and means that the value may vary by 10%, preferably no more than 5%, and most preferably no more than 2%.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence.

A gene encoding SFK, whether genomic DNA or CDNA, can be isolated from any source, particularly from a human CDNA (or INST) or genomic library. In view and in conjunction with the present teachings, methods well known in the art, as described above can be used for obtaining SFK genes from any source (see, e.g., Sambrook el al., 1989, supra).

Accordingly, any animal cell potentially can serve as the nucleic acid source for the molecular cloning of a SFK gene. The DNA may be obtained by standard procedures known in the art from cloned DNA (e.g., a DNA "library"), and preferably is obtained from a CDNA library prepared from tissues with high level expression of the protein by chemical synthesis, by CDNA cloning, or by the cloning of genomic DNA, or fragments thereof, purified from the desired cell (See, for example, Sambrook et al., 1989, supra; Glover, D.M. (ed.), 1985, DNA Cloning: A Practical Approach, MRL Press, Ltd., Oxford, U.K. Vol. 1, II). Clones derived from genomic DNA may contain regulatory and intron DNA regions in addition to coding regions; clones derived from cDNA will not contain intron sequences. Whatever the source, the gene can be molecularly cloned into a suitable vector for propagation of the gene.

In the molecular cloning of the gene from genomic DNA, DNA fragments are generated, some of which will encode the desired gene. Thc DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired SFK gene may be accomplished in a number of ways. For example, if an amount of a portion of a SSFK gene or its specific RNA, or a fragment thereof, is available and can be purified and labeled, the generated DNA fragments may be screened by nucleic acid hybridization to the labeled probe [Benton and Davis, *Science,* 196:180 (1977); Grunstein and Hogness, *Proc. Natl. Acad. Sci. U.S.A.,* 72:3961 (1975)]. For example, a set of oligonucleotides corresponding to the partial amino acid sequence information obtained for the SFK protein can be prepared and used as probes for DNA encoding SFK, as was done in a specific example, infra, or as primers for CDNA or mRNA (e.g., in combination with a poly-T primer for RT-PCR). Preferably, a fragment is selected that is highly unique to SFK of the invention. Those DNA fragments with substantial homology to the probe will hybridize. As noted above, the greater the degree of homology, the more stringent hybridization conditions can be used. In a specific embodiment, stringency hybridization conditions are used to identify a homologous SFK gene.

Further selection can be carried out on the basis of the properties of the gene, e.g., if the gene encodes a protein product having the isoelectric, electrophoretic, amino acid composition, or partial amino acid sequence of SFK protein as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e. ., has similar or identical electrophoretic migration, isoelectric focusing or non-equilibrium pH gel electrophoresis behavior, proteolytic digestion maps. or antigenic properties as known for SFK.

A SFK gene of the invention can also be identified by mRNA selection, i.e., by nucleic acid hybridization followed by in vitro translation. In this procedure, nucleotide fragments are used to isolate complementary mRNAs by hybridization. Such DNA fragments may represent available, purified SFK DNA, or may be synthetic oligonucleotides designed from the partial amino acid sequence information. Immunoprecipitation analysis or functional assays (e.g., kinase activity) of the in vitro translation products of the products of the isolated mRNAs identifies the mRNA and. therefore, the complementary DNA fragments, that contain the desired sequences. In addition, specific mRNAs may be selected by adsorption of polysomes isolated from cells to immobilized antibodies specifically directed against SFK, such as the rabbit polyclonal anti-murine SFK antibody described herein.

A radiolabeled SFK CDNA can be synthesized using the selected mRNA (from the adsorbed polysomes) as a template. The radiolabeled mRNA or CDNA may then be used as a probe to identify homologous SFK DNA fragments from among other genomic DNA fragments.

The genes encoding SFK derivatives and analogs of the invention can be produced by various methods known in the art. The manipulations which result in their production can occur at the gene or protein level. For example, the cloned SFK gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of SFK, care should be taken to ensure that the modified gene remains within the same translational reading frame as the SFK gene, uninterrupted by translational stop signals, in the gene region where the desired activity is encoded.

Additionally, the SFK-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated SFK gene product. Any technique for mutagenesis known in the art can be used, including but not limited to, in vitro site-directed mutagenesis [Hutchinson, et all., *J Biol. Chem.,* 253:6551 (1978); Zoller and Smith, *DNA,* 3:479–488 (1984); Oliphant el al., *Gene.* 44:177 (1986); Hutchinson el al., *Proc. Natl. Acad. Sci. U.S.A.,* 83:710 (1986)], use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification,* H. Erlich, ed., Stockton Press, Chapter 6, pp. 61–70).

The present invention also relates to cloning vectors containing genles encoding analogs and derivatives of SFK of the invention, that have the same or homologous functional activity as SFK, and homologs thereof from other species. The production and use of derivatives and analogs related to SFK are within the scope of the present invention. In a specific embodiment, the derivative or analog is functionally active, i.e., capable of exhibiting one or more functional activities associated with a full-length, wild-type SFK of the invention. In another aspect, a SFK protein of the invention can be prepared by substituting the SH2 (and/or SH3) domain(s) with that of a related src-family kinase.

SFK derivatives can be made by altering encoding nucleic acid sequences by substitutions, additions or deletions that provide for functionally equivalent molecules. Preferably, derivatives are made that have enhanced or increased kinase activity relative to native SFK.

Due to the degeneracy of nucleotide coding sequences, other DNA sequences which encode substantially the same amino acid sequence as a SFK gene may be used in the practice of the present invention. These include but are not limited to allelic genes, homologous genes from other species, and nucleotide sequences comprising all or portions of SFK genes which are altered by the substitution of different codons that encode the same amino acid residue within the sequence, thus producing a silent change.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli,* bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporationi, etc., so that many copies of the gene sequence are genierated. Preferably, the cloned gene is contained on a shuttle vector plasmid, which provides for expansion in a cloning cell, e.g., *E. coli,* and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2µ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of SFK Polypeptidcs

The nucleotide sequence coding for SFK, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding SFK of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding SFK and/or its flanking regions.

Potential lost-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA. plasmid DNA, or cosmid DNA. The expression elements of vectors vary in their strengths and specificities. Depending on the host-vector system utilized, any one of a number of suitable transcription and translation elements may be used.

A recombinant SFK protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook el al., 1989, supra).

The cell containing the recombinant vector comprising the nucleic acid encoding SFK is cultured in an appropriate cell culture medium under conditions that provide for expression of SFK by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of SFK protein may be controlled by any promoter/enhancer element known in the art, but these regulatory elements must be functional in the host selected for expression. Promoters which may be used to control SFK gene expression include, but are not limited to, the SV40 early promoter region [Benoist and Chambon. *Nature,* 290:304–310 (1981)], the promoter contained in the 3' long terminal repeat of Rous sarcoma virus [Yamamoto et al., *Cell,* 22:787–797 (1980)], the herpes thymidine kinase promoter [Wagner et al., *Proc. Natl. Acad. Sci. U.S.A.,* 78:1441–1445 (1981)], the regulatory sequences of the metallothionein gene [Brinster et al., *Nature,* 296:39–42 (1982)1; prokaryotic expression vectors such as the β-lactamase promoter [Villa-Kamaroff et al., *Proc. Natl. Acad. Sc. U.S.A.,* 75:3727–3731 (1978)], or the tac promoter [DeBoer el al., *Proc. Natl. Acad. Sci. U.S.A.,* 80:21–25 (1983)]; see also "Useful proteins from recombinant bacteria" in Scientific American, 242:74–94 (1980); promoter elements from yeast or other fungi such as the Gal 4 promoter, the ADC (alcohol dehydrogenase) promoter, PGK (phosphoglycerol kfinase) promoter, alkaline phosphatase promoter; and the animal transcriptional control regions, which exhibit tissue specificity and have been utilized in transgenic animals: elastase I gene control region which is active in pancreatic acinar cells [Swift et al., *Cell,* 38:639–646 (1984); Ornitz et al., *Cold Spring Harbor Symp. Quant. Biol.,* 50:399–409 (1986); MacDonald, *Hepatology,* 7:425–515 (1987)]; insulin gene control region which is active in pancreatic beta cells [Hanahan, *Nature,* 315:115–122 (1985), immunoglobulin gene control region which is active in lymphoid cells [Grosschedl et al., *Cell,* 38:647–658 (1984); Adames et al., Nature, 318:533–538 (1985); Alexander et al., *Mol. Cell. Biol.,* 7:1436–1444 (1987)], mouse mammary tumor virus control region which is active in testicular, breast, lymphoid and mast cells [Leder et al., *Cell,* 45:485–495 (1986)], albumin gene control region which is active in liver [Pinkert el al., *Genes and Devel.,* 1:268–276 (1987)], alplha-fetoprotein gene control region which is active in liver [Krumlauf et al., *Mol. Cell.*

Biol., 5:1639–1648 (1985); Hammer et al., Science, 235:53–58 (1987)], alpha 1-antitrypsin gene control region which is active in the liver [Kelsey et al., Genes and Devel., 1:161–171 (1987)], beta-globin gene control region which is active in mycloid cells [Mogram el al., Nature, 315:338–340 (1985); Kollias et al. Cell, 46:89–94 (1986)], myelin basic protein gene control region which is active in oligodendrocyte cells in the brain [Readhead et al., Cell, 48:703–712 (1987)], myosin light chain-2 gene control region which is active in skeletal muscle [Sani, Nature, 314:283–286 (1985)], and gonadotropic releasing hormone gene control region which is active in the hypothalamus [Mason el al., Science, 234:1372–1378 (1986)].

Expression vectors containing a nucleic acid encoding a SFK of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding SFK is inserted within the "selection marker" gene sequence of the vector, recombinants containing the SFK insert can be identified by the absence of the SFK gene function. In the fourth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasiuids, e.g., E. coli plasmids col E1, pCR1, pBRR322, pMB9 and their derivatives, plasmids such as RP4; phage DNAS, e.g., the numerous derivatives of phage λ, e.g., NM989, and other phage DNA, e.g., M13 and Filamentous single stranded phage DNA; yeast plasmids such as the 2µ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the ARC system, the LTR system, the major operator and promoter regions of phage λ, the control regions of fd coat protein, the promoter for 3-phosphoglycerate kinase or other glycolytic enzymes, the promoters of acid phosplhatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukalyotic and prokaryotic hosts, such as strains of E. coli, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, Such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

In a specific embodiment, an SFK fusion protein or peptide can be expressed. A SFK fusion protein comprises at least a functionally active portion of a non-SFK protein joined via a peptide bond to a SFK or a fragment of a SFK. Similarly a SFK fusion peptide can be expressed. The non-SFK sequences can be amino- or carboxyl-terminal to the SFK sequences. For stable expression of a SFK fusion protein, the portion of the non-SFK fusion protein or peptide can be joined via a peptide bond to the amino terminus of the SFK protein. A recombinant DNA molecule encoding such a fusion protein comprises a sequence encoding at a functionally active portion of a non-SFK protein or peptide joined in-frame to the SFK coding sequence, and preferably encodes a cleavage site for a specific protease, e.g., thrombin or Factor Xa, preferably at the SFK-non-SFK juncture. Such a cleavage site can be used in the ultimate purification of the SFK, e.g., when the heterologous amino acid sequence portion of the fusion protein is used as a ligand for a affinity column.

In a specific embodiment, the fusion protein is expressed in Escherichia coli. An example of a fusion peptide is a SFK having a FLAG-tag. An example of a fusion protein is a SFK or a fragment thereof joined with a green fluorescent protein or modified green fluorescent protein as described in U.S. Pat. No. 5,625,048, Issued Apr. 29, 1997 herein incorporated by reference in its entirety. Such fusion proteins and peptides may also be classified as chimeric proteins or peptides.

It is further intended that SFK analogs may be prepared from nucleotide sequences of the protein complex/subunit derived within the scope of the present invention.

Analogs, such as fragments, may be produced, for example, by pepsin digestion of SFK material. Other analogs, such as muteins, can be produced by standard site-directed mutagenesis of SFK coding sequences. Analogs exhibiting "SFK activity" such as small molecules, whether functioning as promoters or inhibitors, may be identified by known in vivo and/or in vitro assays.

As mentioned above, a DNA sequence encoding a SFK can be prepared synthetically rather than cloned. The DNA sequence can be designed with the appropriate codons for the SFK amino acid sequence. In general, one will select preferred codons for the intended host if the sequence will be used for expression. The complete sequence is assembled from overlapping oligonucleotides prepared by standard methods and assembled into a complete coding sequence. See e.g., Edge, Nature, 292:756(1981); Nambair el al, Science, 223:1299 (1984); Jay el., J. Biol. Chem., 259:6311 (1984).

Synthetic DNA sequences allow convenient construction of genes which will express SFK analogs or "muteins". Alternatively, DNA encoding muteins can be made by site-directed mutagenesis of native SFK genes or cDNAs, and muteins can be made directly using conventional polypeptide synthesis.

A general method for site-specific incorporation of unnatural amino acids into proteins is described in Christopher J. Noren, Spencer J. Anthony-Cahill. Michael C. Griffith, Peter G. Schultz, Science, 244:182–188 (April 1989). This method may be used to create analogs with unnatural amino acids.

Antibodies

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoolobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protcin mercaptan with a reagent such as iodoacetamide. An antibody containing intact antibody molecules is preferred herein.

The phrase "monoclonal antibody" in its various (grammatical forms refers to an antibody having only one species of antibody combining site capable of immunoreactinig with a particular antigen. A monocloial antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier el al., "Hybridoma Techniques" (1980); Hammerling el al., "Monoclonal Antibodies And T-cell Hybridomas" (1981); Kennett el al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against SFSK peptides can be screened for various properties; i.e., isotype, epitope, affinity, etc. Of particular interest arc monoclonal antibodies that neutralize the binding activity of the SFK or its subunits.

Such monoclonals can be readily identified in, for example, gel-shift assays. High affinity antibodies are also useful when immunoaffinity purification of native or recombinant SFK is possible.

Preferably, the anti-SFK antibody used in the diagnostic methods of this invention is an affinity purified polyclonal antibody. More preferably, the antibody is a monoclonal antibody (mAb). In addition, it is preferable for the anti-SF K antibody molecules used herein be in the form of Fab, Fab', F(ab')$_2$ or F(v) portions of whole antibody molecules.

Methods for producing polyclonal anti-polypeptide antibodies are well-known in the art. See U.S. Pat. No. 4,493, 795 to Nestor el al. A monoclonal antibody, typically containing Fab and/or F(ab')$_2$ portions of useful antibody molecules, can be prepared using the hybridoma technology described in Aulibodies—A Laborctiory Acanual, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a SFK-binding portion thereof, or SFK, or a DNA-binding portion thereof.

Splenocytes are typically fused with myeloma cells using polyethylene glycol (PEG) 6000. Fused hybrids are selected by their sensitivity to HAF. Hybridomas producing a monoclonal antibody useful in practicing this invention are identified by their ability to immunoreact with the present SFK.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic muedium is Dulbecco's minimal essential medium (DMEM; Dulbecco el al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal anti-SFK antibodies are also well-known in the art. See Niman el al., *Proc. Natl. Acad. Sci. USA,* 80:4949–4953 (1983). Typically, the present SFK or a peptide analog is used either alone or conjugated to an immunogenic carrier, as the immunogen in the before-described procedure for producing anti-SFK monoclonal antibodies. The hybridomas are screened for the ability to produce an antibody that immunloreacts with the SFK peptide analog and the present SFK.

Diagnostics and Therapeutics

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to significantly ameliorate a symptom caused by an abnormal *laloo,* or a deficiency/overexpression of *laloo* (e.g., a 20% improvement).

The possibilities both diagnostic and therapeutic that arc raised by the existence of *laloo,* derive from the fact that *laloo* has substantial homology with known proto-oncogenes and furthermore plays an important role in signal transduction in the embryogenisis. As suggested earlier and elaborated further on herein, the present invention contemplates pharmaceutical intervention in the cascade of events in which the SFK of the present invention is implicated, to modulate the activity mediated by this important signal transducer.

As discussed earlier, the SFKs of the present invention or their binding partners or other ligands or agents exhibiting either mimicry or antagonism to the SFK or control over their production, may be prepared in pharmaceutical compositions, with a suitable carrier and at a strength effective for administration by various means to a patient experiencing an adverse medical condition associated with the abnormal expression of *laloo* for the treatment thereof. A variety of administrative techniques may be utilized, among them topological, or alternatively parenteral techniques such as subcutaneous, intravenous and intraperitoneal injections, catheterizations and the like. Average quantities of the SFKs may vary and in particular should be based upon the recommendations and prescription of a qualified physician or veterinarian.

Also, antibodies including both polyclonal and monoclonal antibodies, and drugs that modulate the production or activity of the SFKs of the present invention may possess certain diagnostic applications and may for example, be utilized for the purpose of detecting and/or measuring conditions such as precancerous conditions or the like. For example, the SFKs of the present invention or its structural/functional domains may be used to produce both polyclonal and monoclonal antibodies to themselves in a variety of cellular media, by known techniques such as the hybridoma technique utilizing, for example, fused mouse spleen lymphocytes and myeloma cells.

Likewise, small molecules that mimic or antagonize the activity(ies) of the SFK of the invention may be discovered or synthesized, and may be used in diagnostic and/or therapeutic protocols.

As suggested earlier, the diagnostic method of the present invention comprises examining a cellular sample or medium by means of an assay including an effective amount of an antagonist to a SFK protein, such as an anti-SFK antibody, preferably an affinity-purified polyclonal antibody, and more preferably a mAb. In addition, it is preferable for the anti-SFK antibody molecules used herein be in the form of Fab, Fab', F(ab')$_2$ or F(v) portions or whole antibody molecules. As previously discussed, patients capable of benefiting from this method include those suffering from cancer, a pre-cancerous lesion, or other like pathological derangement. Methods for isolating and inducing anti-SFK antibodies and for determining and optimizing the ability of anti-SFK antibodies to assist in the examination of the target cells are all well-known in the art.

The present invention further contemplates therapeutic compositions useful in practicing the therapeutic methods of this invention. A subject therapeutic composition includes, in admixture, a pharmaceutically acceptable excipient (carrier) and one or more of a SFK of the present invention, polypeptide analog thereof or fragment thereof, as described herein as an active ingredient. In a preferred embodiment, the composition comprises an antigen capable of modulating the specific binding of *laloo* within a target cell.

The preparation of therapeutic compositions which contain polypeptides, analogs or active fragments as active ingredients is well understood in the art. Typically, such compositions are prepared as topological agents or alternatively as injectables, either as liquid solutions or suspensions, however, solid forms suitable for solution in, or suspension in, liquid prior to injection (or topological administration) can also be prepared. The preparation can also be emulsified. The active therapeutic ingredient is often mixed with excipients which are pharmaceutically acceptable and compatible with the active ingredient. Suitable excipients are, for example, distilled water, saline, dextrose, glycerol, ethanol, or the like and combinations thereof. In addition, if desired, the composition can contain minor amounts of auxiliary substances Such as wetting or emulsifying agents, pH buffering a(gents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine. procaine, and the like.

The therapeutic polypeptide-, analog- or active fragment-containing compositions are conventionally administered topologically or alternatively, intravenously as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of *laloo* desired. Precise amounts of active ingredient required to be administered depend on the judgment of the practitioner and are peculiar to each individual.

However, suitable dosages may range from about 0.1 to 20, preferably about 0.5 to about 10, and more preferably one to several, micrograms of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration.

The present invention also relates to a variety of diagnostic applications, including methods for detecting the presence of stimuli such as the earlier referenced polypeptide ligands, by reference to their ability to elicit the activities which are mediated by the SFKs of the present invention. As mentioned earlier, the SFKs of the present inventions can be used to produce antibodies to itself by a variety of known techniques, and such antibodies could then be isolated and utilized as in tests for the presence of particular activity of *laloo* in suspect target cells.

Assays for Agonists and Antagonists of SFKs and Kits

Identification and isolation of a gene encoding a SFK of the invention provides for expression of SFK in quantities greater than can be isolated from natural sources, or in indicator cells that are specially engineered to indicate the activity of SFK expressed after transfection or transformation of the cells. Accordingly, in addition to rational design of agonists and antagonists based on the structure of the SFK of the present invention, the present invention further contemplates an alternative method for identifying specific ligands of SFK using various screening assays known in the art.

Any screening technique known in the art can be used to screen for SFK agonists or antagonists. The present invention contemplates screens for small molecules that bind to the SFKs of the present invention and agonize or antagonize *laloo* in vitro and/or in vivo. For example, natural products libraries can be screened using assays of tile invention for molecules that agonize or antagonize the activity of *laloo*.

Knowledge of the primary sequence of the SFKs of the present invention, and the similarity of that sequence with other src-family tyrosine kinases, can provide an initial clue as to the likely structural properties for an inhibitor or antagonist of *laloo*.

Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, Science 249:386–390 (1990); Cwirla, et al., Proc. Nail. Acad Sci., 87:6378–6382 (1990); Deylin et al., Science, 249:404–406 (1990)], very large libraries can be constructed ($10^6$–$10^8$ chemical entities). A second approach uses primarily chemical methods, of which the Geysen method [Geysen et al., Molecular Immunology 23:709–715 (1986); Geysen et al. *J. Immunologic Method* 102:259–274 (1987)] and the method of Fodor et al. [*Science* 251:767–773 (1991)] are examples. Furka el al. [*14th International Congress of Biochemistry, Volume 5*, Abstract FR:013 (1988); Furka, *Int. J Peptide Protein Res.* 37:487–493 (1991)], Houghton [U.S. Pat. No. 4,631,211, issued December 1986] and Rutter et al. U.S. Pat. No. 5,010,175, issued Apr. 23, 1991] describe methods to produce a mixture of peptides that can be tested as agonists or antagonists.

In another aspect, synthetic libraries [Needels et al., *Proc. Natl. Acad. Sci. USA* 90:10700–4 (1993); Ohlmeyer et al., *Proc. Natl. Acad. Sci. USA* 90:10922–10926 (1993); Lam et al., International Patent Publication No. WO 92/00252; Kocis et al., International Patent Publication No. WO 9428028. each of which is incorporated herein by reference in its entirety], and the like can be used to screen for SFK ligands (e.g., binding partners) according to the present invention.

Screening can be performed with recombinant cells that express the SFKs of the present invention, or alternatively, using purified protein, and/or specific structural/functional domains of the SFKs e.g., produced recombinantly, as described above. For example, a labeled SFK can be used to screen libraries, as described in the foregoing references for small molecules that will inhibit the kinase activity of SFK.

The effective peptide(s) can be synthesized in large quantities for use in in vivo models and eventually in humans to modulate *laloo* signal transduction. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success IPatarroyo, Vaccine 10:175–178 (1990)].

In a further embodiment of this invention, commercial test kits suitable for use by a medical specialist may be prepared to determine the presence or absence of *laloo* activity in suspected target cells. In accordance with the testing techniques discussed above, one class of such kits will contain at least a labeled SIFK of the present invention or its binding partner, for instance an antibody specific thereto, and directions, of course, depending upon the method selected, e.g., "competitive", "sandwich", "DASP" and the like. The kits may also contain peripheral reagents such as buffers, stabilizers, etc.

Accordingly, a test kit may be prepared for the demonstration of the presence of *laloo*, or a nucleic acid encoding a *laloo* comprising:

(a) a predetermined amount of at least one labeled immunochemically reactive component obtained by the direct or indirect attachment of an SFK of the present invention to a detectable label, or alternatively, a labeled anti-*laloo* antibody, or a labeled nucleic acid probe which can hybridize to a nucleic acid encoding a *laloo* with specificity;

(b) other reagents; directions for use of the kit can also be included.

In one particular embodiment, the diagnostic test kit may comprise:

(a) a known amount of the SFK as described above (or a binding partner such as an anti-*laloo* antibody) generally bound to a solid phase to form an immunosorbent, or in the alternative, bound to a suitable tag, or plural such end products, etc. (or their binding partners) one of each;

(b) if necessary, other reagents; directions for use of the test kit can also be provided.

In a further variation, the test kit may be prepared and used for the purposes stated above, which operates according to a predetermined protocol (e.g. "competitive", "sandwich", "double antibody", etc.), and comprises:

(a) a labeled component which has been obtained by coupling *laloo* to a detectable label;

(b) one or more additional immunochemical reagents of which at least one reagent is a ligand or an immobilized ligand, selected from the group consisting of:

(i) a ligand capable of binding with the labeled component of (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; again directions can be provided for the performance of a protocol for the detection and/or determination of one or more components of an immunochemical reaction between *laloo* and a specific binding partner thereto.

In accordance with the above, an assay system for screening potential drugs effective to modulate the activity of the SFKs of the present invention may also be prepared. In one such method a potential drug that modulates the ability of an SFK of the present invention to induce the transcription of mesodermal markers is identified. First an mRNA encoding the SFK is injected into an animal pole of a 2-cell stage embryo in the presence of an agent (i.e., a potential drug). Next the the animal pole explant is isolated at the late blastula stage. The animal pole explant is then cultured until midgastrula or late neurula stages. After extracting the RNA from the animal pole explant the transcription of a mesodermal marker protein is assayed. By comparing the amount of transcription in the presence of the agent relative to in its absence, an agent is identified as a potential drug when the agent enhances or diminishes the transcription relative to in its absence. The assaying of the transcription of the mesodermal marker may be performed by any of a number of means but is preferably determined by reverse transcriptase polymerase chain reaction (RT-PCR). In one such embodiment the 2-cell stage embryo is a xenopus embryo. Appropriate mesodermal markers include Xbra. Xwnt8, HoxB9, and muscle actin.

Labels

The SFKs of the present inventions, fragments thereof, and their antibodies, nucleic acids encoding the SFKs, the specific domains of SFKs, and probes to the nucleic acids may all be labeled The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The SFKs of the present invention or its binding partner (s) can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodlimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus pcroxidase and alkaline phosphatase. U.S. Pat. Nos. 3,654,090; 3,850,752; and 4,016,043 are referred to by way of example for their disclosure of alternate labeling material and methods. In addition, green fluorescent protein and derivatives thereof, as exemplified in U.S. Pat. No. 5,625.048 Issued 4/29/97 and International Publication No: WO 97/26333. hereby incorporated by reference in their entireties, can also be used.

Antisense, Gene Targeting and Ribozymes

The functional activity of SFK can be evaluated transgenically. In this respect, a transgenic mouse model can be used. The SFK gene can be used in complementation studies employing transgenic mice. Transgenic vectors, including viral vectors, or cosmid clones (or phage clones) corresponding to the wild type locus of candidate gene, can be constructed using the isolated SFK gene. Cosmids may be introduced into transgenic mice using published procedures [Jacnisch, *Science,* 240:1468–1474 (1988)]. In a genetic sense, the transgene acts as a suppressor mutation.

Alternatively, a transgenic animal model can be prepared in which expression of the SEK gene is disrupted. Gene expression is disrupted, according to the invention, when no functional protein is expressed. One standard method to evaluate the phenotypic effect of a gene product is to employ knock-out technology to delete the gene. Knock-out technology to delete a gene is described in U.S. Pat. No. 5,464,764, Issued Nov. 7, 1995; and U.S. Pat. No. 5,777, 195, Issued Jul. 7, 1998 (both of which are hereby incorporated by reference herein in their entireties.)

The present invention also extends to the preparation of antisense nucleotides and ribozymes that may be used to interfere with the expression of the SFKs of the present invention at the translational level. This approach utilizes antisense nucleic acid and ribozymes to block translation of a specific mRNA, either by masking that MRNA with an antisense nucleic acid or cleaving it with a ribozyme.

Antisense nucleic acids are DNA or RNA molecules that are complementary to at least a portion of a specific mRNA molecule [See Weintraub, *Sci. Amer.* 262:40–46 (1990); Marcus-Sekura, *Nucl. Acid Res,* 15: 5749–5763 (1987); Marcus-Sekura *Anal. Biochem.,* 172:289–295 (1988); Brysch el al., *Cell Mol. Neurobiol.,* 14:557–568 (1994)]. Preferably, the antisense molecule employed is complementary to a substantial portion of the mRNA. In the cell, the antisense molecule hybridizes to that mRNA, forming a double stranded molecule. The cell does not translate an MRNA in this double-stranded form. Therefore, antisense nucleic acids interfere with the expression of mRNA into protein. Preferably a DNA antisense nucleic acid is employed since such an RNA/DNA duplex is a preferred substrate for RNase H. Oligomers of greater than about fifteen nucleotides and molecules that hybridize to the AUG initiation codon will be particularly efficient, though larger molecules that are essentially complementary to the entire mRNA are more likely to be effective. Antisense methods have been used to inhibit the expression of many genes in vitro [Marcus-Sekura, Anal. Biochem., 172:289–295 (1988); Hambor el al., *Proc. Natl. Acad. Sci. U.S.A.* 85:4010–4014 (1988)] and in situ [Arima et al, *Antisense Nucl. Acid Driug Dev.* 8:319–327 (1998); Hou et al., *Antisense Nacl. Acid Drug Dev.* 8:295–308 (1998)].

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these ribozymes, researchers have been able to engineer molecules that recognize specific nucleotide sequences in an RNA molecule and cleave it [Cech, *JAMA,* 260:3030–3034 (1988); Cech, *Biochem. Intl,* 18:7–14 (1989)]. Because they are sequence-specific, only mRNAs with particular sequences arc inactivated.

Investigators have identified two types of ribozymes, Tetrahymena-type and "hammerhead"-type [Haselhoff and Gerlach, *Nature* 334:585–591 (1988)]. Tetrahyrnena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to 7etrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs encoding the SFKs of the present invention.

Gene Therapy and Transgenic Vectors

In one embodiment, a gene encoding a SFK of the present invention is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, any tissue can be specifically targeted. Examples of particular vectors include, but are not limited to, a defective herpes virus 1 (HSV1) vector [Kaplitt et al., *Molec. Cell. Neurosci.* 2:320–330 (1991)], an attenuated adenovirus vector, such as the vector described by Stratford-Perricaudet et al. [*J. Clin. Invest.* 90:626–630 (1992)], and a defective adeno-associated virus vector [Samulski et al., *J. Virol.* 61:3096–3101 (1987); Samulski et al., *J. Virol.* 63:3822–3828(1989)].

Preferably, for in vitro administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, *Nature Medicine* (1995)]. In addition, it is advantageous to employ a viral vector that is engineered to express a minimal number of antigens.

In another embodiment the gene can be introduced in a retroviral vector, e.g. as described in Anderson et al. U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; International Patent Publication No. WO 95/07358, published March 16, 1995, by Dougherty et al.; and Kuo et al., 1993. Blood 82:845. Targeted gene delivery is described in International Patent Publication WO 95/28494, published October 1995.

Alternatively, the vector can be introduced in vil o by lipofection. 1 or the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vitro transfection of a gene encoding a marker [Fclgner, et. al., *Proc. Natl. Acad. Sci. U.S.A.* 84:7413–7417 (1987); see Mackey, et al., *Proc. Natl. Acad. Sci. U.S.A.* 85:8027–8031 (1988)]. The use of cationic lipids may promote encapsulation of negatively charged nucleic acids, and also promote fusion with negatively charged cell membranes [Feigner and Ringold, *Science* 337:387–388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or nonpeptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAF dextran, calcium phosphate precipitation, use of a (gene gun, or use of a DNA vector transporter [see, e.g., Wu el at., *J. Biol. Chem.* 267:963–967 (1992); Wu and Wu, *J. Biol. Chem.* 263:14621–14624 (1988); Hartmut et al. Canadian Patent Application No. 2,012,311, filed Mar. 15, 1990].

In a preferred embodiment of the present invention, a gene therapy vector as described above employs a transcription control sequence operably associated with the sequence for the SFKs of the present invention inserted in the vector. That is, a specific expression vector of the present invention can be used in gene therapy. Such an expression vector is particularly useful to regulate expression of a therapeutic SFK gene. In one embodiment, the present invention contemplates constitutive expression of the SFK gene, even if at low levels.

The present invention may be better understood by reference to the following non-limiting Example, which is provided as exemplary of the invention. The following example is presented in order to more fully illustrate the

EXAMPLE

MESODERM INDUCTION BY LALOO, A NOVEL SRC-FAMILY KINASE

Summary

The src family of non-receptor tyrosine kinases have been implicated in the control of cell growth and differentiation in numerous experimental systems. Reported herein is the isolation of a novel src-family kinase from Xenopus laevis; named herein laloo. During Xenopus embryogenesis, laloo mRNA is widely expressed, and is present both as a maternal and a zygotic transcript. Ectopic expression of laloo induces mesoderm in Xenopus ectoderm cultures; this induction is blocked by reagents that disrupt the Fibroblast Growth Factor (FGF) signaling pathway. Conversely, overexpression of a kinase-defective laloo mutant blocks induction by soluble FGF. These results indicate an essential role for src-family kinases in mesoderm induction by FGF. Experiments using, a hyperactive laloo mutant more precisely placed this activity within the FGF signal transduction pathway.

Materials and Methods

Library Construction and Screening:

Early gastrula (stage 10) Xenopus laevis embryos were homogenized with RNAzol B solution and processed according to the manufacture's instructions (Tel-Test, Inc.). 4.5 ug of polyA+RNA was selected from 2.4 mg of total RNA using the OLIGOTEX mRNA midi kit by Qiagen. cDNA synthesis and linker addition was performed using the Superscript 11 unidirectional Kit (Gibco BRL). After second-strand synthesis, cDNAs were size-selected by gel filtration and subcloned in a modified pCS2 vector (average size: 2.0 kb). $2 \times 10^6$ transformants were obtained after electroporationl in ElectroMAX DH10B cells (GIBCO BRL).

The library was plated in order to obtain approximately 1000 clones per initial pool. For subsequent sib selection, 10 pools of five-fold fewer clones were screened (e.g., 10×200, 10×50, etc.). Pooled plasmid DNA was linearized with AscI. RNA was synthesized using the mMessage mMachine kit (Ambion). Embryos were injected with 10 nl of 0.5 mg/ml pooled RNA into animal poles of both blastomeres at the 2-cell stage.

Sequence analysis was carried out using the DNA Strider and DNA Star software packages and the NIH BLAST program.

RNA Preparation, Microcdissection, Explant Dissection, and Cell Culture:

mRNA was synthesized in vitro in the presence of cap analog using the mMessage mMachine kit (Ambion). RNA from all constructs was synthesized using the Sp6 promoter. Microinjection, explant dissection and culture were performed as described in llemmati-Brivanlou and Melton [Nature, 359:609–614 (1992)].

Reverse Transcriptase Polymerase Chain Reactions.

RT-PCR was performed as described in Wilson and Hemmati-Brivanlou [Nature, 376:331–333 (1995)]. Primers constructed for this study are as follows:

```
laloo:  U: 5'-TGGCTCTGTACTGTGATC-3'   (SEQ ID NO.9)

5'-GTCATACAAAGCCAGCAG-3'      (SEQ ID NO.10)
```

All other primer sequences are listed in Hemmati-Brivanlou and Melton [Cell, 77:273–281 (1994)]; Hemmati-Brivanlou et al. [Cell, 77:283–295 (1994)]; and Suzuki et al. [Dev. Biol., 184:402–405 (1997a) and Development, 124:3037–3044 (1997b)]. PCR for Xwnt8, HoxB9, and NCAM were performed for 25 cycles; PCR for laloo, EF1-a, Xbra, chordin, muscle actin, and ODC were performed for 21 cycles.

Laloo Mitutant Construct Preparation:

The laloo mutants K2591E and Y492F were generated by PCR. For K259E, we introduced a point mutation (A—>G) which resulted in a lysine (AAA) to glutamic acid (GAA) mutation in the resulting construct: 5'-GTA GAA ACA ATG AAG CCA GGC AGC (SEQ ID NO:11). For Y492F, we introduced a point mutation (A—>T) which resulted in a tyrosine (TAC) to phenylalanine (TTC) mutation in the resulting construct. The complimentary strand oligo thus includes a T—>A mutation: 5'-TTA AGG TTG TGC CTG GAA CTG (SEQ ID NO:12).

Results

Isolation of Laloo:

In an attempt to isolate factors involved in patterning of the body axis, a plasmid cDNA library from poly(A)+ Xenopus gastrula RNA was constructed and screened.

Figure 1A:
Figure 1B:
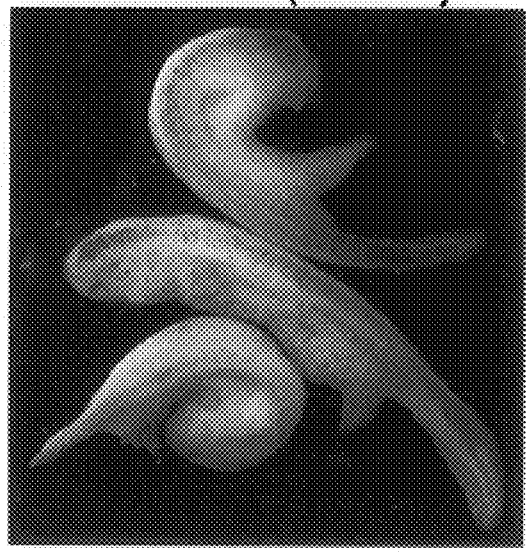

RNA was generated from pools of 200 cDNAs, and injected into the animal poles of embryos at the 2-cell stage. One pool, 27A, gave what appeared to be a secondary tail. Using a sib selection procedure, the clone 27AIJA was isolated, which gives a phenotype similar to what was observed at the pool of 200 (FIGS. 1A–B).

A BLAST homology search revealed that 27AIJA is related to the src family of intracellular tyrosine kinases [Brown and Cooper, Biochimica et Biophysica Acta, 1287:121–149 (1996)] (FIGS. 1C and 1D). The 27AIJA CDNA encodes a novel family member. This clone is more than twice as divergent from its closest amniote relative (hck) than other cloned Xenopus src-family kinases (Xsrc, Xyes, Xfyn, Xlyn) are to their amniote homologs [Brown and Cooper, Biochimica et Biophysica Acta, 1287:121–149 (1996), and references therein]. 27AIJA is also less closely related to amniote hck than is the putative Xenopus homolog of the related lyn gene (sequence ID#: 2114076). This new gene is named laloo, after a 19th century circus performer who had a small, headless twin attached to his breastbone. laloo contains putative src-homology 3 (SH3, amino acids 53–111), src-homology 2 (S112, amino acids 117–210), and kinase domains (amino acids 224–483) domains. These structural motifs are conserved among all src-family proteins [Brown and Cooper, Biochimica et Biophysica Acta, 1287:121–149 (1996)] (FIG. 1C).

Laloo Induces Mesoderm in Ectodermal Explants:

Ectopic laloo expression in the ectoderm induces the formation of tail-like structures. To better define a role for laloo, its function was assayed in an explant assay. Varying doses of laloo RNA were injected into the animal poles of 2-cell stage embryos. At late blastula stages, animal pole explants (animal caps) were isolated and cultured until midgastrula or late neurula stages, at which point RNA was extracted and assayed for the expression of cell-type specific molecular markers by RT-PCR. These animal cap assays demonstrated that overexpression of laloo induces mesoderm in animal caps (FIG. 2). At midgastrula stages, laloo-injected caps express both Xbra, a pan-mesodermal marker, and Xwnt8, a marker of ventrolateral mesoderm [Smith et (it., Cell., 67:79–87 (1991); Smith and Harland, Cell, 67:753–765 (1991)](FIG. 2A, lanes 1–4). In control uninjected caps at this stage, no Xbra or Xwnt8 expression is detected; these caps will go on to form atypical epidermis (FIG. 2A, lane 5). Neither control caps nor laloo-expressing caps contain dorsal mesoderm, as assayed by the expression of the dorsal marker chordin [Sasai et al., *Cell,* 79:779–790 (1994)]. At late neurula stages, *laloo*-expressing caps show strong expression of HoxB9 (X1Hbox6) which, at this stage, is expressed in both lateral mesoderm and the spinal cord [Wright et al., *Development,* 109:225–234 (1990)] (FIG. 2B, lanes 1–4). NCAM, a pan-neural marker, is not induced in these caps [Kintner and Melton, *Development,* 99:311–325 (1987)]; thus, it can be concluded that the HoxB9 expression induced by *laloo* at this stage represents mesodermal, and not neural, tissue. At high doses, *laloo* induces muscle actin expression [Mohun el al., *Nature,* 311:716–721 (1984)] (FIG. 2B, lane 1). Muscle actin is a marker of dorsolateral mesoderm; this result indicates that high levels of *laloo* expression give rise to more dorsal fates than do lower doses. The levels of Xbra, Xwnt8, and HoxB9 expression at active doses of *laloo* remain relatively constant. This is the first report of mesoderm induction by a src-family kinase.

Spatiotemporal Localization of *Laloo*

Mesoderm induction in Xenopus occurs between cleavage and early gastrula stages [Jones and Woodland, *Development,* 101:557–563 (1987)]. To analyze the expression of *laloo,* both during this period and in later development, RT-PCR analysis was performed on embryos harvested between blastula and tadpole stages, using primers specific to *laloo* (FIG. 3). While expression can be detected at all stages assayed, *laloo* expression appears to be divided into two distinct periods: early expression, with *laloo* RNA lost by stage 12.5, and a fully zygotic component which initiates after stage 19. The early peak of *laloo* expression clearly contains a maternal component: *laloo* is expressed in 2-cell stage embryos, hours before the initiation of zygotic transcription. It is possible, however, that *laloo* expression at late blastula and gastrula stages does not include a zygotic component. Widespread, early expression of other Xenopus src family genes has previously been reported [Collett and Steele, *Dev. Biol.,* 152:194–198 (1992)]. Using a combination of whole-mount in situ hybridization and microdissection techniques, no localization of *laloo* expression at any stage examined was observed; thus, *laloo* is ubiquitously expressed du ring early development.

Relationships Between *Laloo*-Mediated Mesoderm Induction and Other Mesoderm-Inducing Pathways:

TGF-β

Members of both the FGF-β and FGF ligand families have been shown capable of inducing mesoderm [Klein and Melton, *Endocr. Rev.,* 15:326–341 (1994)]. Recently, the signaling pathways by which the TGF-β ligands activin and bone morphogenetic proteins (BMPs) induce mesoderm have been elucidated. The intracellular Smad proteins transduce signals from activated TGF-β receptors; Smad4 is a required participant for signaling by both activin and the BMPs, along with Smad2 and Smad1, respectively [Massague et al., *TICB,* 7:187–192 (1997)]. To see if mesoderm induction by *laloo* requires signaling through the Smad pathway, *laloo* was coinjected with tSmad4, a truncated Smad4 shown to block signaling by both Smad1 and Smad2, and induction in animal cap explants was studied [Lagna et al., *Nature,* 383:832–836 (1996)] (FIG. 4). Smad2 transduces signals through the activin receptor, and strongly induces the expression of both Xbra and Xwnt8 at the doses used here (FIG. 4, lane 4). Although tSmad4 is not itself an inducer of mesoderm (FIG. 4, lane 3), coinjection of an equimolar amount of tSmad4 inhibits mesoderm induction by Smad2 (FIG. 4, lane 5). In contrast, tSmad4 does not block Xbra or Xwnt8 induction by *laloo* (FIG. 4, compare lanes 1 and 2). Thus, it can be concluded that the induction of mesoderm by *laloo* acts downstream, or independently, of the Smad proteins.

FGF

The signaling pathway by which FGF mediates mesoderm induction has been extensively characterized [Labonne and Whitman, *Dev. Biol.,* 183:9–20 (1997), and references therein]. To assay for an interaction between *laloo* and components of the FGF pathway, *laloo* was first coexpressed with a dominant-inhibitory form of ras, previously shown to block mesoderm induction by FGF [Whitman and Melton, *Nature,* 357:252–255 (1992)]. Soluble FGF strongly induces the expression of both Xbra and Xwnt8 at the concentrations used (FIG. 5A, lane 5). Dominant-inhibitory ras does not itself induce mesoderm (FIG. 5A, lane 2), and entirely blocks mesoderm induction by FGF (FIG. 5A, lane 6). Dominant-inhibitory ras also blocks induction by *laloo* (FIG. 5A, compare lanes 1 and 3). This result indicates that mesoderm induction by *laloo* requires signaling through the wild-type ras protein.

Mesoderm induction by *laloo* was next challenged with a truncated form of the FGF receptor (XFD), also shown to act as a dominant-inhibitory molecule [Amaya et al., *Cell,* 66:257–270 (1991)] (FIG. 5B). Since *laloo* is a putative intracellular signaling molecule, it might bypass an inhibition by XFD at the cell surface. XFD blocks Xbra and Xwnt8 induction by bFGF, as expected (FIG. 5B, compare lanes 5 and 6), and ectopic XFD does not itself induce mesoderm (FIG. 5B, lane 2). Somewhat surprisingly, XFD blocks the induction of Xbra or Xwnt8 by *laloo* (FIG. 5B, compare lanes 1 and 3). Thus, inhibition of the FGF pathway at the receptor level also blocks mesoderm induction by *laloo.*

Negative Regulation of *Laloo*

In a number of systems, the activity of src family kinases have been shown to be under tight control. All src-related proteins contain a C-terminal tyrosine which, when phosphorylated, dramatically inhibits the activity of the protein [Brown and Cooper, *Biochimica et Biophysica Acta,* 1287:121–149 (1996)]. In order to examine whether similar regulation of *laloo* may occur during early Xenopus development, a mutant form of *laloo* was constructed, in which the putative negative regulatory tyrosine (Y492) was replaced with a phenylalanine. This construct, Y492F, was used in animal cap assays (FIG. 6). Y492F is indeed more active than wild-type *laloo* in the mesoderm induction assay. At midgastrula stages, Y492F induces Xbra and Xwnt8 at lower doses than does wild-type (compare FIGS. 2A and 6A, lanes 1-4). Similarly, at late neurula stages, Y492F induces both HoxB9 and muscle actin at lower doses than does wild-type *laloo* (compare FIGS. 2B and 6B, lanes 1-4). At both early and late stages, Y492F induces more of a given marker at all doses than does the wild-type. As with wild-type *laloo,* expression of Xbra, Xwnt8, or HoxB9 remains relatively constant at active doses of Y492F. Also, as with wild-type *laloo,* an induction of muscle actin (a marker of dorsolateral mesoderm) is observed only at higher doses of Y492F (FIG. 6B, lanes 1 and 2). Thus, as has been shown for other src proteins in other experimental systems, *laloo* activity is modulated through a C-terminal tyrosine residue.

Y492P Bypasses Inhibition by the Truncated FGF Receptor.

As described above, the amino acid Y492 has been identified as a site of negative regulation of *laloo.* Both a truncated FGF receptor and dominant-inhibitory ras have been shown to be capable of blocking mesoderm induction by wild-type *laloo.* The question arose as to whether the inducing ability of the hyperactive mutant Y492F was similarly inhibited by these reagents. As shown earlier, both *laloo* and Y492F induce the mesodermal markers Xbra and Xwnt8 (FIG. 7, lanes 1, 2), both dominant inhibitory ras (dom. inhib. ras) and XFD completely block induction by *laloo* (FIG. 7, lanes 3, 4). Induction by Y492F is also blocked by dominant inhibitory ras (FIG. 7, lane 5); however, Y492F activity is largely unaffected by co-expression of XFD (FIG. 7, lane 6). Thus, while XFD blocks mesoderm induction by *laloo*, the point mutant Y492F bypasses this inhibition.

Mesoderm Induction by *Laloo* Requires an Active Kinase:

In addition to a putative kinase domain, *laloo* contains src homology 2 and src homology 3 (SH2 and SH3) domains, involved in protein-protein interactions. Other molecules that contain only SH2 and SH3 domains have been shown to mediate signaling through receptor tyrosine kinases without themselves possessing enzymatic activity [Lowenstein et al., *Cell*, 70:431–442 (1992)]. It is thus possible that ectopic *laloo* induces mesoderm solely via SH2 and/or SH3 interactions. In order to test for a role of the *laloo* kinase domain in mesoderm induction, a *laloo* mutant was constructed with a disruption in the putative ATP phosphotransferase site [Ziegler et al., *Mol. Cell. Biol.*, 9:2724–2727 (1989)]. This mutant, K259E, was tested in the animal cap assay (FIG. 8A). K259E does not induce either Xbra or Xwnt8 in midgastrula ectoderm explants, even at high doses (FIG. 8A, lane 2). In addition, K259E overexpression did not block mesoderm induction by wild-type *laloo* at 2-fold concentrations over wild-type (FIG. 8A, compare lanes 1 and 3). Thus, *laloo* appears to mediate mesoderm induction via its kinase domain.

Kinase-Defective *Laloo* Inhibits Mesoderm Induction by Soluble Growth Factors:

In cell culture studies, mutants similar to K259E have been shown to act as dominant-negative molecules, blocking signaling through the wild-type kinase [Ziegler et al., *Mol. Cell. Biol.*, 9:2724–2727 (1989); Levin et al., *EMBO J.*, 12:1671–1680 (1993)]. The question arose as to what effect K259E1 might have at blocking other known inducers of mesoderm (FIG. 8B). Treatment of blastula animal caps with soluble bFGF protein induces expression of the ventrolateral mesoderm marker Xwnt8 and the panmesodermal marker Xbra at midgastrula stages (FIG. 8B, lane 4); activin induces these markers as well as the dorsal marker chordin (FIG. 8B, lane 6). Injection of high doses (2–4 ng) of kinase-defective K259E at the 2-cell stage blocks induction of both Xbra and Xwnt8 by bFGF (FIG. 8B, compare lanes 3 and 4), and blocks induction of Xbra, but not Xwnt8 or chordin, by activin (FIG. 8B, compare lanes 5 and 6). This result suggests that signaling through wild-type *laloo*, or a related factor, is required for mesoderm induction by bFGF, and is also required for some aspects of mesoderm induction by activin.

Conclusion

Using a series of gain- and loss-of-function experiments, the role for *laloo* in FGF-mediated mesoderm induction has been demonstrated. First, the dominant inhibitory ras completely blocks mesoderm induction by *laloo*. It has been shown that other src-family kinases transmit signals through ras [Brown and Cooper, *Biochimica et Biophysica Acta*, 1287:121–149 (1996)]. The molecular interactions proposed to link src-family kinases to ras are several, and may include phosphorylation of shc and/or rasGAP [Rozakis-Adcock et al., *Nature*, 360:689–692 (1992); Ellis et al., *Nature*, 343:377–381 (1990)].

Second, XFD blocks induction by *laloo*, but has no effect on the *laloo* mutant Y492F. These results indicate that the mesoderm-inducing activity of ectopic *laloo* is dependent upon a basal level of signaling through the FGF receptor, and that this requirement is mediated through tyrosine 492 of *laloo*. It has been demonstrated in numerous systems that the C-terminal tyrosine in src-family proteins is an important site of negative regulation [Brown and Cooper, *Biochimica et Biophysica Acta*, 1287:121–149 (1996)]. Conversely, it has been shown that phosphatases can stimulate the activity of these molecules. For example, in lymphocytes, the CD45 receptor-like membrane phosphatase activates the src-family kinase lck [Weiss and Littman, *Cell*, 76:263–274 (1994)]. Ectopic *laloo* may become heavily phosphorylated in the animal cap assays described herein, and thus is only active in the presence of some level of FGF-mediated phosphatase activity. Interestingly, inhibition of the SH2-containing phosphatase SH-PTP2 blocks mesoderm induction by FGF [Tang et al., *Cell*, 80:473–483 (1995)]. Thus, in vivo, the activated FGF receptor may activate SH-PTP2 or a related phosphatase, which in turn could activate *laloo* via dephosphorylation of Y492.

Finally, overexpression of a kinase-defective *laloo* point mutant (K259E) blocks mesoderm induction by bFGF. K259E and *laloo* presumably share the same substrate specificity; K259E, however, will not phosphorylate *laloo* substrates, and overexpression of the mutant may sequester targets of endogenous, activated *laloo*.

The wild-type *laloo* does not inhibit induction by bFGF or activin, arguing for the specificity of inhibition by K259L. The inability of K259E to block Xwnt8 induction by activin is inconsistant with a global repression by the mutant.

The block to mesoderm induction by K259E suggests that FGF signal transduction requires endogenous *laloo*. This observation is bolstered by data from other systems: in cell culture, inhibition of src-family kinase activity has also been shown to block the effects of several receptor tyrosine kinases (RTKs), including the FGF receptor; furthermore, several src-family proteins have been shown to physically interact with the platelet-derived growth factor (PDGF) RTK [Kypta el al., *Cell*, 62:481–492 (1990); Kremer et al., *J. Cell. Biol.*, 115:809–819 (1991); Twamley-Stein et al., *Proc. Natl. Acad. Sci. USA*. 90:7696–7700 (1993)].

Although mesoderm induction by *laloo* is not inhibited by tSmad4, the kinase-defective *laloo* mutant, K259E, strongly inhibits the activin-mediated induction of Xbra, and fails to block Xwnt8 induction by activin. This partial inhibition suggests that *laloo* may mediate aspects of activin signaling downstream of the Smad proteins. Recent work has demonstrated a link between the Smad proteins and the MAP kinase pathway downstream of the epidermal growth factor (EGF) receptor and other RTKs: stimulation of the EGF pathway inhibits nuclear accumulation and transcriptional activation by Smad1 [Kretzschmar et. al., *Nature*, 389:618–622 (1997)]. *Laloo* induces mesoderm, however, and thus is not likely to inhibit signaling by Smad1 or Smad2. Rather, the partial inhibition of activin by K259E is likely to be secondary to a block of FCF signaling. Other groups have shown that inhibition of the FGF pathway blocks the induction of some mesodermal genes by activin: the failure of K259E to inhibit Xwnt8 induction by activin is reminiscent of effects seen with inhibitors of the FGF pathway. For example, Xwnt8, unlike Xbra, is induced in XFD-expressing animal caps treated with activin [Cornell and Kimelman, *Development*, 120:453–462 (1994); LaBonne and Whitman, *Development*, 120:463–472 (1994)]. This indicates that at least one "FGF-independent,"

activin-inducible gene, Xwnt8, is also "*laloo*-independent." Thus, the K259E-mediated block to Xbra induction by activin is consistent with a block to the FGF pathway.

Functional redundancy has been described among src-family kinases in other systems [Brown and Cooper, *Biochimica et Biophysica Acta,* 1287:121–149 (1996)]; other, related kinases are likely to share latoo's mesoderm-inducing abilities. Several Xenopus src-family kinases, other than *laloo*, are also expressed during early development [Steele, *Nucleic Acids Res.,* 13:1747–1761 (1985); Steele et al., *Oncogene Res.,* 1:223–233 (1989); Steele el al., *Oncogene,* 5:369–376 (1990)]. A constitutively active form of src, however, is apparently not capable of inducing mesoderm, pointing to some degree of specificity among these factors during development [Whitman and Melton, *Nature,* 376:331–333 (1992)]. Other workers have shown that nck, an intracellular SH2–SH3 containing adaptor molecule, ventralizes Xenopus mesoderm, but does not induce it [Tanaka el al., *Proc. Natl. Acad. Sci. USA,* 94:4493–4498 (1997)]. Although nck lacks a catalytic domain, kinase defective *laloo* does not ventralize mesoderm (FIG. 7B); thus, the SH2–SH3 domains of nck and *laloo* likely bind distinct factors. The present results provide strong evidence that a src-family kinase plays a critical, and previously unsuspected, role during early vertebrate embryogenesis.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are hereby incorporated by reference in their entireties.

What is claimed is:

1. An antibody which specifically binds to a polypepitde comprising the amino acid sequence of SEQ ID NO:2.

2. The antibody of claim 1 which is a polyclonal antibody.

3. The antibody of claim 1 which is a monoclonal antibody.

4. An immortal cell line that produces the monoclonal antibody of claim 3.

5. The antibody of claim 1 that is a chimeric antibody.

6. An antibody according to claim 1 which specifically binds to a domain of the polypeptide, the domain being selected from the group consisting of:

(a) a catalytic tyrosine kinase domain;

(b) a src-homology-2 domain; and (c) a src-homology-3 domain.

7. An antibody according to claim 6 which specifically binds to a catalytic tyrosine kinase domain of the polypeptide, wherein the catalytic tyrosine kinase domain comprises the amino acid sequence of SEQ ID NO:8.

8. An antibody according to claim 6 which specifically binds to a src-homology-2 domain of the polypeptide, wherein the src-homology-2 domain comprises the amino acid sequence of SEQ ID NO:6.

9. An antibody according to claim 6 which specifically binds to a src-homology-3 domain of the polypeptide, wherein the src-homology-3 domain comprises the amino acid sequence of SEQ ID NO:4.

10. An antibody which specifically binds to an antigen selected from the group consisting of:

(a) a src-family-kinase (SFK) having the amino acid sequence of SEQ ID NO:2;

(b) a src-homology-3 domain of a SFK, which src-homology-3 domain has the amino acid sequence of SEQ ID NO:4;

(c) a src-homology-2 domain of a SFK, which src-homology-2 domain has the amino acid sequence of SEQ ID NO:6;

(d) a catalytic tyrosine kinase domain of a SFK, which catalytic tyrosine kinase domain has the amino acid sequence of SEQ ID NO:8;

(e) a SFK having the amino acid sequence of SEQ ID NO:2, further comprising the amino acid substitution Y492F; and (f) a SFK having the amino acid sequence of SEQ ID NO:2, further comprising the amino acid substitution K259E.

11. The antibody of claim 10 wherein the antigen is part of a chimeric or fusion protein.

12. The antibody of claim 10 which is a polyclonal antibody.

13. The antibody of claim 10 that is a chimeric antibody.

14. The antibody of claim 10 which is a monoclonal antibody.

15. An immortal cell line that produces the monoclonal antibody of claim 14.

16. The antibody of claim 10 wherein the antigen is a SFK having the amino acid sequence of SEQ ID NO:2.

17. The antibody of claim 10 wherein the antigen is a src-homology-3 domain of a SFK, which src-homology-3 domain has the amino acid sequence of SEQ ID NO:4.

18. The antibody of claim 10 wherein the antigen is a src-homology-2 domain of a SFK, which src-homology-2 domain has the amino acid sequence of SEQ ID NO:6.

19. The antibody of claim 10 wherein the antigen is a catalytic tyrosine kinase domain of a SFK, which catalytic tyrosine kinase domain has the amino acid sequence of SEQ ID NO:8.

20. The antibody of claim 10 wherein the antigen is a SFK having the amino acid sequence of SEQ ID NO:2 and further comprising the amino acid substitution Y492F.

21. The antibody of claim 10 wherein the antigen is a SFK having the amino acid sequence of SEQ ID NO:2 and further comprising the amino acid substitution K259E.

* * * * *

UNITED STATES PATENT AND TRADEMARK OFFICE
CERTIFICATE OF CORRECTION

PATENT NO. : 6,291,651 B1
DATED : September 18, 2001
INVENTOR(S) : Ali Hemmati-Brivanlou and Daniel C. Weinstein It is certified that error appears in the above-identified patent and that said Letters Patent is hereby corrected as shown below:

<u>Title page,</u>
Item [75] Inventor, change
"Ali Hemmait-Brivanlou" should be -- Ali Hemmati-Brivanlou --.
Item [73] Assignee, change
"The Rockerfeller University" should be -- The Rockefeller University --.

Signed and Sealed this

Thirtieth Day of April, 2002

Attest:

JAMES E. ROGAN
*Director of the United States Patent and Trademark Office*

*Attesting Officer*